(12) United States Patent
Ueyama

(10) Patent No.: US 7,477,933 B2
(45) Date of Patent: Jan. 13, 2009

(54) PORTABLE ELECTROCARDIOGRAPH, ELECTROCARDIOGRAM MONITORING SYSTEM, AND ELECTROCARDIOGRAM MONITORING METHOD USING THE SAME

(75) Inventor: Kenji Ueyama, Hirakata (JP)

(73) Assignee: Sanyo Electric Co., Ltd., Osaka (JP)

( * ) Notice: Subject to any disclaimer, the term of this patent is extended or adjusted under 35 U.S.C. 154(b) by 85 days.

(21) Appl. No.: 10/695,442

(22) Filed: Oct. 29, 2003

(65) Prior Publication Data

US 2004/0138575 A1 Jul. 15, 2004

(30) Foreign Application Priority Data

Oct. 31, 2002 (JP) ............... 2002-318766
Oct. 31, 2002 (JP) ............... 2002-318767

(51) Int. Cl.
*A61B 5/0428* (2006.01)
*A61B 5/0432* (2006.01)

(52) U.S. Cl. ............... 600/509; 607/36; 607/60
(58) Field of Classification Search ............ 600/509, 600/300, 513; 607/36, 60
See application file for complete search history.

(56) References Cited

U.S. PATENT DOCUMENTS

| | | | | |
|---|---|---|---|---|
| 5,674,260 | A * | 10/1997 | Weinberg | 607/36 |
| 5,861,019 | A * | 1/1999 | Sun et al. | 607/60 |
| 6,282,441 | B1 * | 8/2001 | Raymond et al. | 600/513 |
| 6,287,252 | B1 * | 9/2001 | Lugo | 600/300 |
| 6,289,238 | B1 * | 9/2001 | Besson et al. | 600/509 |
| 6,485,416 | B1 | 11/2002 | Platt et al. | |
| 6,544,173 | B2 | 4/2003 | West et al. | |
| 6,544,174 | B2 | 4/2003 | West et al. | |
| 6,602,191 | B2 * | 8/2003 | Quy | 600/300 |
| 7,225,029 | B2 * | 5/2007 | Shankar et al. | 607/60 |
| 2001/0039372 | A1 | 11/2001 | Yasushi et al. | |
| 2002/0091331 | A1 | 7/2002 | Onoda et al. | |
| 2002/0107453 | A1 | 8/2002 | Matsumura et al. | |
| 2003/0109905 | A1 * | 6/2003 | Mok et al. | 607/60 |
| 2005/0107714 | A1 | 5/2005 | Matsumura et al. | |
| 2005/0119580 | A1 | 6/2005 | Matsumura et al. | |
| 2005/0119581 | A1 | 6/2005 | Matsumura et al. | |
| 2005/0119582 | A1 | 6/2005 | Matsumura et al. | |
| 2005/0143669 | A1 | 6/2005 | Matsumura et al. | |

FOREIGN PATENT DOCUMENTS

EP 1 188 412 3/2002

(Continued)

*Primary Examiner*—George R Evanisko
*Assistant Examiner*—Michael Kahelin
(74) *Attorney, Agent, or Firm*—McDermott Will & Emery LLP

(57) ABSTRACT

Electrocardiogram data and acceleration data obtained by a portable electrocardiograph of each patient are transmitted to a radio base station, and transmitted from the radio base station to a hospital computer via a public network, a line L, and a TA. Electrocardiograms and accelerations of a plurality of patients are displayed on the screen of the hospital computer based on the electrocardiogram data and acceleration data in real time. In the portable electrocardiograph, a communication device and an interface unit for communication are separated from other components by a ground plane, and an electrocardiogram measurement device is separated from the other components by a ground plane. Two of the ground planes are provided between the communication device and the interface unit for communication and the electrocardiogram measurement device.

9 Claims, 18 Drawing Sheets

FOREIGN PATENT DOCUMENTS

| | | | |
|---|---|---|---|
| JP | 02-299632 A | 12/1990 | |
| JP | 04-371134 A | 12/1992 | |
| JP | 05-298589 A | 11/1993 | |
| JP | 09-289974 A | 11/1997 | |
| JP | 10-137210 | 5/1998 | |
| JP | 10-165385 | 6/1998 | |
| JP | 11-70086 | 3/1999 | |
| JP | P2000-279385 | 10/2000 | |
| JP | 2001-046349 A | 2/2001 | |
| JP | 2001-078974 A | 3/2001 | |
| JP | 2001-198096 A | 7/2001 | |
| JP | P2001-510697 | 8/2001 | |
| JP | 2001-258858 A | 9/2001 | |
| JP | P2001-258857 | 9/2001 | |
| JP | 2001-314386 A | 11/2001 | |
| JP | P2002-143097 | 5/2002 | |
| JP | 2002-177232 A | 6/2002 | |
| JP | 2002-224053 A | 8/2002 | |
| JP | 2002-245167 A | 8/2002 | |
| JP | 2002-282218 A | 10/2002 | |

* cited by examiner

F I G. 5
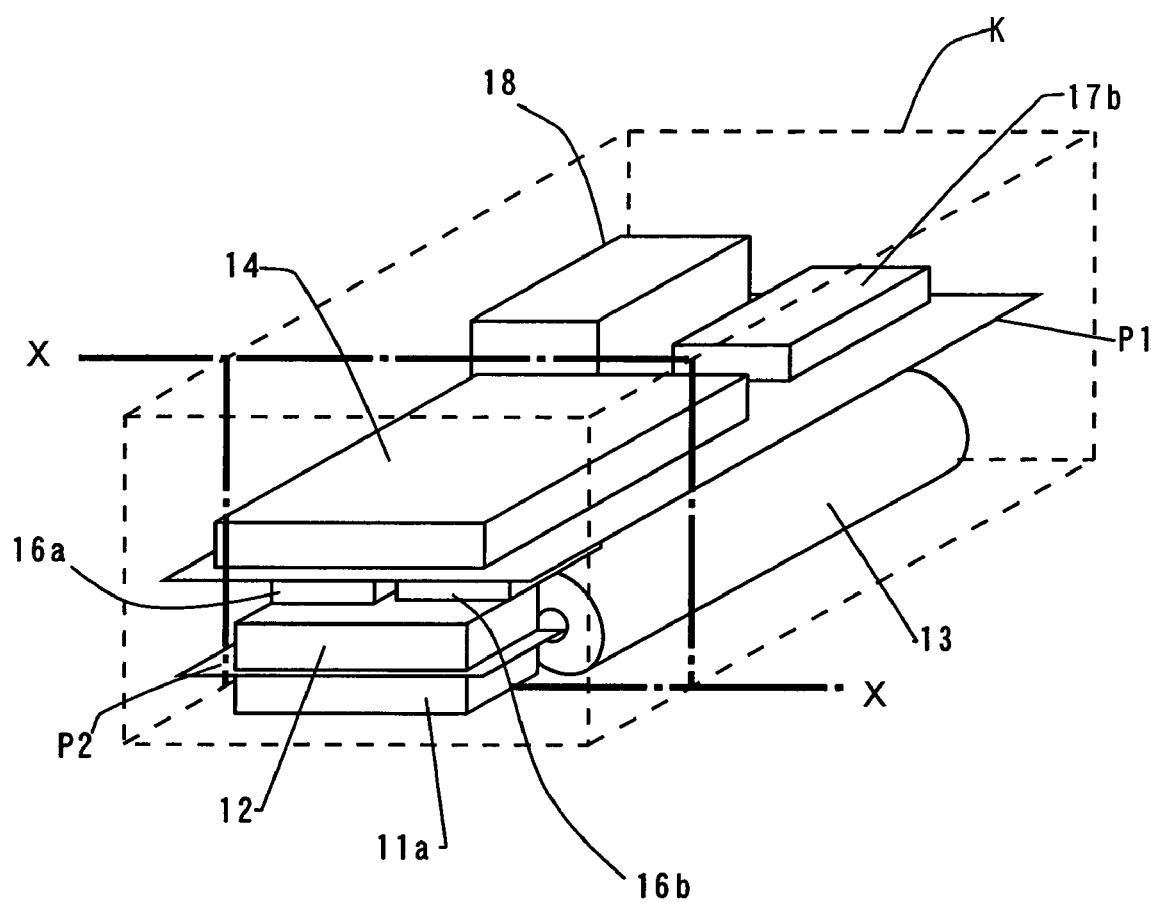

F I G. 9
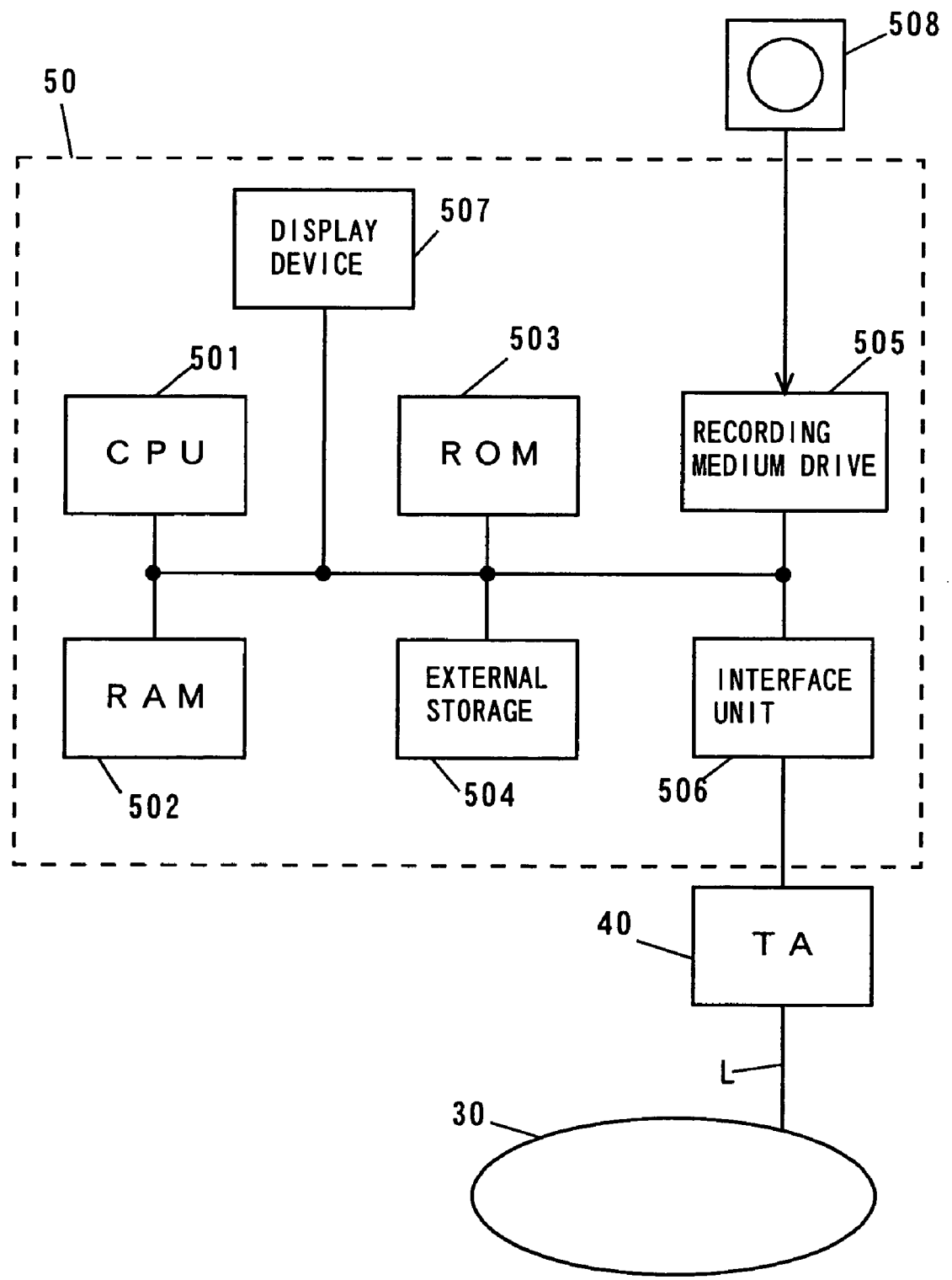

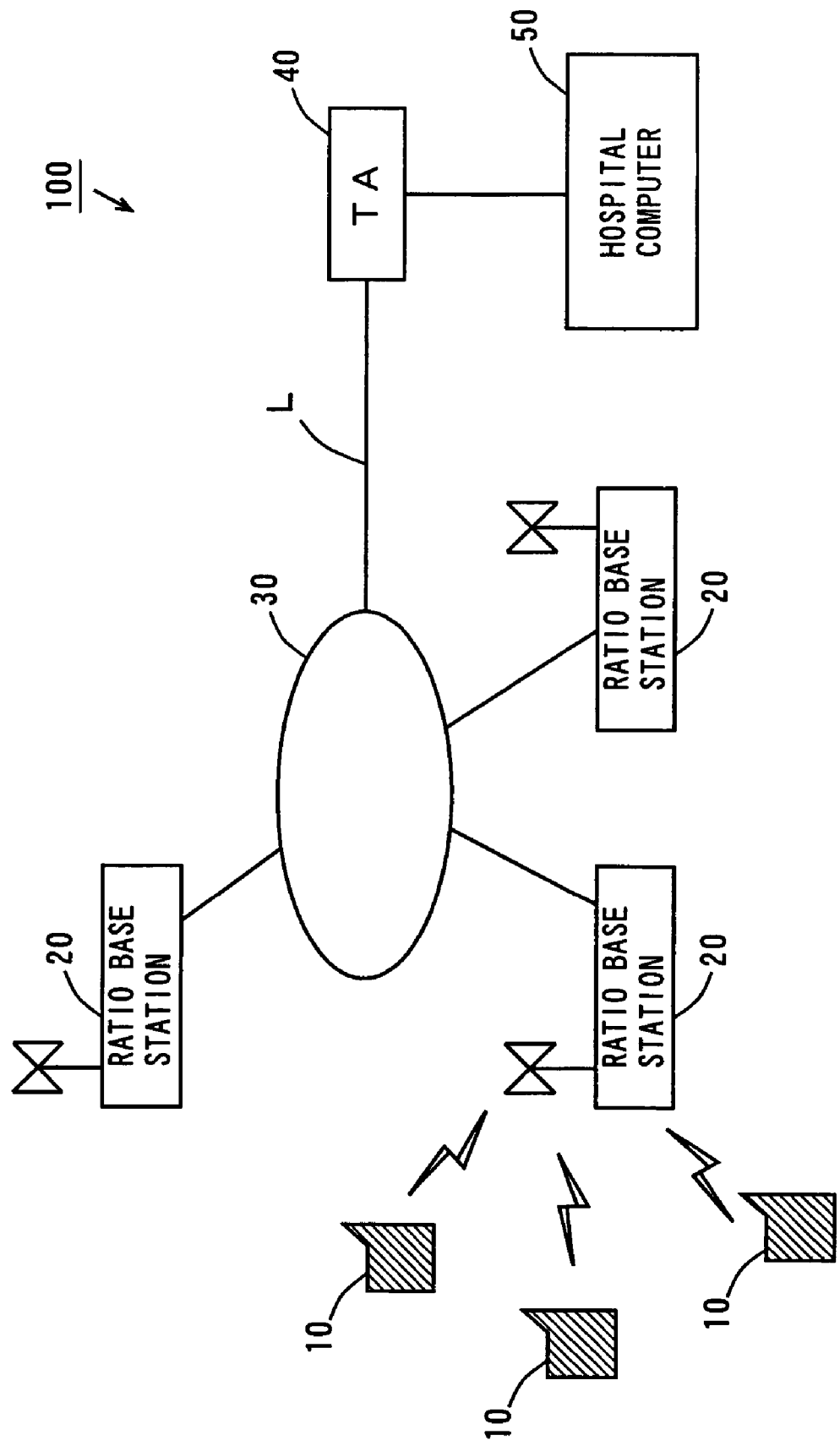

PORTABLE ELECTROCARDIOGRAPH, ELECTROCARDIOGRAM MONITORING SYSTEM, AND ELECTROCARDIOGRAM MONITORING METHOD USING THE SAME

BACKGROUND OF THE INVENTION

1. Field of the Invention

The present invention relates to a portable electrocardiograph capable of measuring an electrocardiogram by being carried by a patient, an electrocardiogram monitoring system and an electrocardiogram monitoring method using the same.

2. Description of the Background Art

A portable electrocardiograph is used for a patient having a heart disease to measure an electrocardiogram as he/she leads an everyday life (see, for example JP 2000-279385 A and JP H10-165385 A). This portable electrocardiograph has a function of storing an electrocardiogram of 24 hours of a patient in a memory card as electrocardiogram data. The patient sends the memory card that stores the electrocardiogram data to a diagnostician, such as a doctor or nurse, and the diagnostician makes a diagnosis based on the electrocardiogram data stored in the memory card that is sent. In recent years, portable electrocardiographs connected to a mobile telephone and having a function of transmitting the electrocardiogram data stored in a memory card to the hospital over a telephone line have also been developed.

Meanwhile, therapeutic exercises are being practiced in hospitals by patients, each having monitored by a diagnostician his/her electrocardiogram. During such exercises, one diagnostician accompanies one patient for a diagnosis of the electrocardiogram of the patient, and the diagnostician can stop the patient's exercise when he/she is in bad condition.

However, in the method in which a patient uses the aforementioned portable electrocardiograph to measure his/her electrocardiogram in every day life, the diagnostician makes a diagnosis later based on the electrocardiogram data stored in a memory card. Therefore, the diagnostician cannot immediately stop the patient's exercise as he/she monitors the electrocardiogram of the patient when the patient is in bad condition.

In addition, one diagnostician is occupied with one patient during the aforementioned therapeutic exercise in hospitals. Since the patients having a heart disease are recently on the increase, it is becoming difficult to continue such therapeutic exercises.

SUMMARY OF THE INVENTION

The object of the present invention is to provide a portable electrocardiograph capable of accurately transmitting the measurement result of the electrocardiogram of a patient in real time.

Another object of the present invention is to provide an electrocardiogram monitoring system and an electrocardiogram monitoring method capable of real time and centralized monitoring of a plurality of patients.

A portable electrocardiograph according to one aspect of the present invention comprises: a stacked-layered circuit board; an electrocardiogram measurement device that measures an electrocardiogram to obtain electrocardiogram data; and a radio communication device that radio-transmits the electrocardiogram data obtained by the electrocardiogram measurement device in real time, the stacked-layered circuit board including a plurality of circuit boards and a ground conductor layer provided between any ones of the plurality of circuit boards, the electrocardiogram measurement device being arranged on one side of the stacked-layered circuit board, and the radio communication device being arranged on the other side of the stacked-layered circuit board.

In the portable electrocardiograph according to the present invention, the electrocardiogram is measured by the electrocardiogram measurement device to obtain the electrocardiogram data. Further, the electrocardiogram data obtained by the electrocardiogram measurement device is radio-transmitted by the radio communication device in real time.

In the portable electrocardiograph according to the present invention, the electrocardiogram measurement device is arranged on one side of the stacked-layered circuit board including the plurality of circuit boards and the ground conductor layer provided between ones of the plurality of circuit boards, and the radio communication device is arranged on the other side of the stacked-layered circuit board. Accordingly, the electrocardiogram measurement device and the radio communication device are isolated from each other by the ground conductor layer during the radio transmission, and the radio waves emitted from the radio communication device are prevented from reaching the electrocardiogram measurement device by the ground conductor layer provided between any ones of the plurality of circuit boards. Therefore, the electrocardiogram measurement device can accurately measure an electrocardiogram based on the faint voltage generated in a human body without being affected by the radio waves emitted from the radio communication device.

Furthermore, in the portable electrocardiograph according to the present invention, the electrocardiogram can be accurately measured by the electrocardiogram measurement device, while the electrocardiogram data can be radio-transmitted in real time by the radio communication device. Therefore, by transmitting the electrocardiogram data to a diagnostician in the hospital, the diagnostician who has received the electrocardiogram data can monitor the electrocardiogram of a patient in real time.

The portable electrocardiograph may further comprise a casing that houses the electrocardiogram measurement device, radio communication device, and stacked-layered circuit board. In this case, the electrocardiogram measurement device, radio communication device, and stacked-layered circuit board are housed in the casing. Accordingly, the radio communication device and electrocardiogram measurement device are integrally housed inside the casing, leading to smaller size and further portability of the portable electrocardiograph.

The portable electrocardiograph may further comprise a first storage device that stores the electrocardiogram data obtained by the electrocardiogram measurement device. In this case, the electrocardiogram data obtained by the electrocardiogram measurement device is stored in the first storage device.

Therefore, even in the case where the electrocardiogram data obtained by the electrocardiogram measurement device is not normally radio-transmitted, with the accurate electrocardiogram data stored in the first storage device, the patient can receive an accurate diagnosis by submitting to the diagnostician the first storage device in which the electrocardiogram data is stored after the measurement of the electrocardiogram.

The portable electrocardiograph may further comprise an accelerometer that measures acceleration to obtain acceleration data, and the radio communication device may radio-transmit the acceleration data obtained by the accelerometer in real time. In this case, the acceleration is measured by the accelerometer to obtain the acceleration data. Further, the acceleration data obtained by the accelerometer is radio-transmitted in real time by the radio communication device.

The acceleration data is accordingly radio-transmitted in real time by the radio communication device. Therefore, the diagnostician who receives the acceleration data can monitor the exercise condition of a patient in real time.

The portable electrocardiograph may further comprise a second storage device that stores the acceleration data obtained by the accelerometer. In this case, the acceleration data obtained by the accelerometer is stored in the second storage device.

Therefore, even in the case where the acceleration data obtained by the acceleration measurement device is not normally radio-transmitted, with the accurate acceleration data stored in the second storage device, a patient can receive an accurate diagnosis by submitting to the diagnostician the second storage device in which the acceleration data is stored after the measurement of the acceleration.

In the portable electrocardiograph, the radio communication device may receive a given alarm signal, and the portable electrocardiograph may further comprise an alarm sound output device that outputs an alarm sound in response to the alarm signal received by the radio communication device. In this case, the diagnostician transmits the alarm signal to the radio communication device when he/she determines that the patient is in bad condition based on the electrocardiogram. When the radio communication device receives the given alarm signal from the diagnostician, the alarm sound is output by the alarm sound output device. In this manner, when the patient is in bad condition, the diagnostician can immediately instructs him/her to stop the exercise via the portable electrocardiograph.

In the portable electrocardiograph, the radio communication device may receive a given alarm signal, and the portable electrocardiograph may further comprise an alarm display device that displays an alarm in response to the alarm signal received by the radio communication device. In this case, the diagnostician transmits the alarm signal to the radio communication device when he/she determines that the patient is in bad condition based on the electrocardiogram. When the radio communication device receives the given alarm signal from the diagnostician, the alarm is displayed by the alarm display device. In this manner, when the patient is in bad condition, the diagnostician can immediately instructs him/her to stop the exercise via the portable electrocardiograph.

An electrocardiogram monitoring system according to another aspect of the present invention comprises: a portable electrocardiograph housing an electrocardiogram measurement device that measures an electrocardiogram to obtain electrocardiogram data, a communication device that radio-transmits the electrocardiogram data obtained by the electrocardiogram measurement device in real time, and a storage device that stores the electrocardiogram data obtained by the electrocardiogram measurement device; and a computer that receives the electrocardiogram data transmitted from the portable electrocardiograph and has a display unit that displays the received electrocardiogram data.

In the electrocardiogram monitoring system according to the present invention, the electrocardiogram data of a patient obtained by the electrocardiogram measurement device in the portable electrocardiograph is radio-transmitted in real time by the communication device in the portable electrocardiograph. The electrocardiogram data transmitted by the portable electrocardiograph is received by the computer, and then the electrocardiogram is displayed on the display unit based on the received electrocardiogram data. The diagnostician can thus make a diagnosis while performing real time and centralized monitoring of the electrocardiogram which is displayed on the display unit in the computer.

Accordingly, the real time and centralized monitoring of the electrocardiogram(s) and acceleration(s) of one or more patients can be realized. Therefore, when a patient measures an electrocardiogram using the portable electrocardiograph in every day life, the diagnostician monitors the electrocardiogram and acceleration of the patient in real time, and can immediately stop the patient's exercise when the patient is in bad condition. In addition, the diagnostician can perform the real time and centralized monitoring of the electrocardiograms of a plurality of patients during their therapeutic exercises in the hospital.

The portable electrocardiograph may further house a storage device. In this case, the electrocardiogram data obtained by the electrocardiogram measurement device in the portable electrocardiograph is stored in the storage device. Therefore, even in the case where the electrocardiogram data obtained by the electrocardiogram measurement device is not normally radio-transmitted, with the accurate electrocardiogram data stored in the storage device, the patient can receive an accurate diagnosis by submitting to the diagnostician the storage device in which the electrocardiogram data is stored after the measurement of the electrocardiogram.

The communication device may be a radio communication device that radio-transmits the electrocardiogram data to a base station connected to a public network, and the computer may include a communication equipment that receives the electrocardiogram data transmitted from the base station via the public network.

In this case, the electrocardiogram data is radio-transmitted to the base station by the radio communication device in the portable electrocardiograph, and is received by the communication equipment in the computer from the base station via the public network. Accordingly, the diagnostician can make a diagnosis while performing real time and centralized monitoring of the electrocardiogram(s) of one or more patients.

The communication equipment may receive the electrocardiogram data transmitted from the base station via the public network via a line. In this case, the electrocardiogram data transmitted by the portable electrocardiograph is transmitted from the base station to the communication equipment via the public network and the line. The computer can thus receive the electrocardiogram data transmitted by the portable electrocardiograph via the communication equipment in real time. Accordingly, the diagnostician can make a diagnosis while performing real time and centralized monitoring of the electrocardiogram(s) of one or more patients.

The communication equipment may receive by radio communication the electrocardiogram data transmitted from the base station to other base station via the public network. In this case, the electrocardiogram data transmitted by the portable electrocardiograph is transmitted from the base station to the other base station via the public network, and then is radio-transmitted from the other base station to the communication equipment. The computer can thus receive the electrocardiogram data transmitted by the portable electrocardiograph via the communication equipment in real time. Accordingly, the diagnostician can make a diagnosis while performing real time and centralized monitoring of the electrocardiogram(s) of one or more patients.

The communication equipment may receive the electrocardiogram data transmitted from the base station via the public network by way of Internet. In this case, since the communication equipment is connected to the public network via the Internet, the computer can receive the electrocardiogram data transmitted by the portable electrocardiograph via the communication equipment in real time. Consequently, the diagnostician can make a diagnosis while performing real time and centralized monitoring of the electrocardiogram(s) of one or more patients.

The communication device may be a radio communication device that radio-transmits the electrocardiogram data to a base station connected to a private network, and the computer may receive the electrocardiogram data transmitted from the base station via the private network.

In this case, the electrocardiogram data is radio-transmitted to the base station by the radio communication device in the portable electrocardiograph, and is received by the computer from the base station via the public network. Consequently, the diagnostician can make a diagnosis while performing real time and centralized monitoring of the electrocardiogram(s) of one or more patients.

The computer may have a function of transmitting a signal to the portable electrocardiograph, the communication device in the portable electrocardiograph may receive the signal transmitted from the computer, and the portable electrocardiograph may further include an alarm output unit that outputs an alarm based on the signal received by the communication device.

In this case, the diagnostician transmits the signal with the computer when he/she determines that the patient is in bad condition based on the electrocardiogram displayed on the display unit in the computer. When the signal transmitted by the diagnostician with the computer is received by the communication device in the portable electrocardiograph, the alarm sound is output by the alarm output unit based on the received signal. Consequently, when the patient is in bad condition, the diagnostician can immediately instructs him/her to stop the exercise via the portable electrocardiograph.

The portable electrocardiograph may comprise a stacked-layered circuit board and may have a casing that houses the electrocardiogram measurement device, communication device, and stacked-layered circuit board, the stacked-layered circuit board may include a plurality of circuit boards and a ground conductor layer provided between any ones of the plurality of circuit boards, the electrocardiogram measurement device may be arranged on one side of the stacked-layered circuit board, and the communication device may be arranged on the other side of the stacked-layered circuit board.

In this case, the electrocardiogram measurement device is arranged on one side of the stacked-layered circuit board including the plurality of circuit boards and the ground conductor layer provided between any ones of the plurality of circuit boards, and the communication device is arranged on the other side of the stacked-layered circuit board. Accordingly, the electrocardiogram measurement device and communication device are isolated from each other by the ground conductor layer during the radio transmission, and the radio waves emitted from the communication device are prevented from reaching the electrocardiogram measurement device by the ground conductor layer provided between any ones of the plurality of circuit boards. Therefore, the electrocardiogram measurement device can accurately measure an electrocardiogram based on the faint voltage generated in a human body without being affected by the radio waves emitted from the communication device.

Furthermore, the electrocardiogram measurement device, communication device, storage device, and stacked-layered circuit board are housed in the casing. Accordingly, the communication device and electrocardiogram measurement device are integrally housed inside the casing, leading to smaller size and further portability of the portable electrocardiograph.

The portable electrocardiograph may further house an acceleration measurement device that measures acceleration to obtain acceleration data, the communication device may radio-transmits the acceleration data obtained by the acceleration measurement device in real time, and the computer may receive the acceleration data transmitted from the portable electrocardiograph to display the acceleration on the display unit based on the received acceleration data.

In this case, the acceleration is measured by the acceleration measurement device to obtain the acceleration data. The acceleration data obtained by the acceleration measurement device is radio-transmitted by the communication device in real time. The transmitted acceleration data is then displayed on the display unit in the computer. Consequently, the diagnostician can make a diagnosis while performing real time and centralized monitoring of the conditions of the exercises of a plurality of patients.

An electrocardiogram monitoring method according to still another aspect of the present invention comprises the steps of: operating a portable electrocardiograph housing an electrocardiogram measurement device and a communication device; measuring an electrocardiogram with the electrocardiogram measurement device to obtain electrocardiogram data; radio-transmitting the electrocardiogram data obtained by the electrocardiogram measurement device through the communication device in real time; receiving the electrocardiogram data transmitted from the portable electrocardiograph by a computer to display the electrocardiogram on a display unit based on the received electrocardiogram data.

In the electrocardiogram monitoring method according to the present invention, the electrocardiogram data of a patient obtained by the electrocardiogram measurement device in the portable electrocardiograph is radio-transmitted in real time by the communication device in the portable electrocardiograph. The electrocardiogram data transmitted by the portable electrocardiograph is received by the computer, and the electrocardiogram is displayed on the display unit based on the received electrocardiogram data. The diagnostician can thus make a diagnosis while performing real time and centralized monitoring of the electrocardiogram which is displayed on the display unit in the computer.

Accordingly, the real time and centralized monitoring of the electrocardiogram(s) and acceleration(s) of one or more patients can be realized. Therefore, when a patient measures an electrocardiogram using the portable electrocardiograph in every day life, the diagnostician monitors the electrocardiogram and acceleration of the patient in real time and can immediately stop the patient's exercise when he/she is in bad condition. In addition, the diagnostician can perform the real time and centralized monitoring of the electrocardiograms of a plurality of patients during their therapeutic exercises in the hospital.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIG. 5 is a schematic perspective view showing one example of the inner structure of the portable electrocardiograph according to the first embodiment;

FIG. 9 is a block diagram showing the structure of a hospital computer in the electrocardiogram monitoring system using the portable electrocardiograph according to the first embodiment;

FIG. 18 is a block diagram showing another example of the structure of the electrocardiogram monitoring system using the portable electrocardiograph shown in FIG. 3.

DESCRIPTION OF THE PREFERRED EMBODIMENTS

Description will be hereinafter made of a portable electrocardiograph according to the embodiments of the present invention and an electrocardiogram monitoring system using the same with reference to the drawings.

First Embodiment

Figure 1:
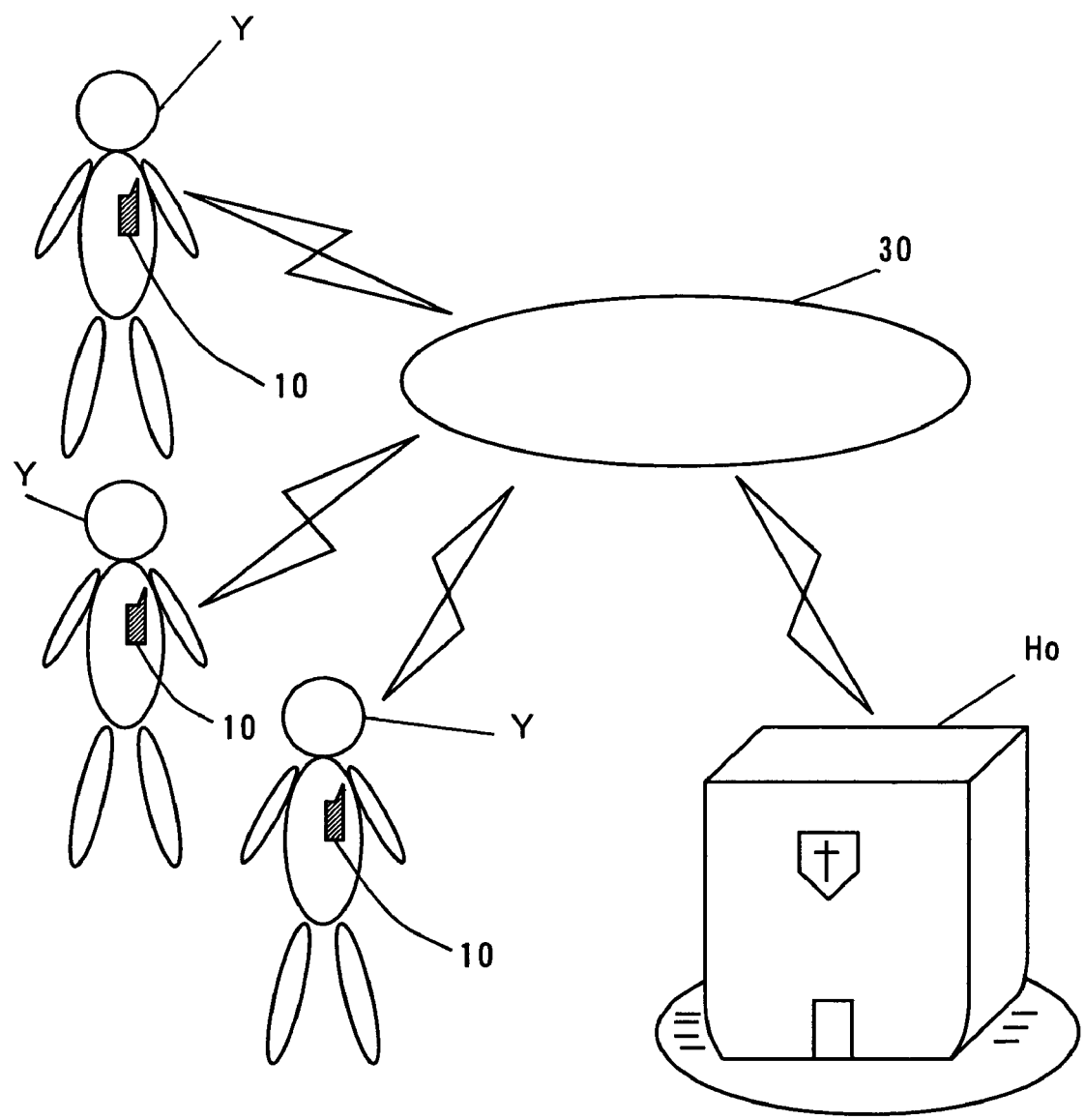
FIG. 1 is a schematic diagram showing the concept of an electrocardiogram monitoring system using a portable electrocardiograph according to a first embodiment.

FIG. 1 is a schematic view showing the concept of an electrocardiogram monitoring system using a portable electrocardiograph according to a first embodiment.

As shown in FIG. 1, each of patients Y attaches a portable electrocardiograph 10 to his/her body prior to the therapeutic exercise. The portable electrocardiograph 10 has an electrocardiogram measurement function, an acceleration measurement function, a data store function, and a data communication function, as described later. Once the patient Y starts the exercise, the electrocardiogram and acceleration of the patient Y are measured by the portable electrocardiograph 10, and the measured electrocardiogram and acceleration are stored as electrocardiogram data and acceleration data in a RAM (Random Access Memory) within the portable electrocardiograph 10, and are also transmitted to a hospital Ho via a public network 30 by the communication function.

The electrocardiograms and accelerations of the plurality of patients Y are displayed on the screen of a computer in the hospital Ho (hereinafter referred to as a hospital computer) based on the electrocardiogram data and acceleration data of the patients Y received in the hospital Ho. A diagnostician such as a doctor or nurse in the hospital thus makes a diagnosis while monitoring the electrocardiogram and acceleration of each of the patients Y in real time, so that he/she can instruct the patient via the portable electrocardiograph 10 to immediately stop the exercise when the patient Y is in bad condition.

Figure 2:
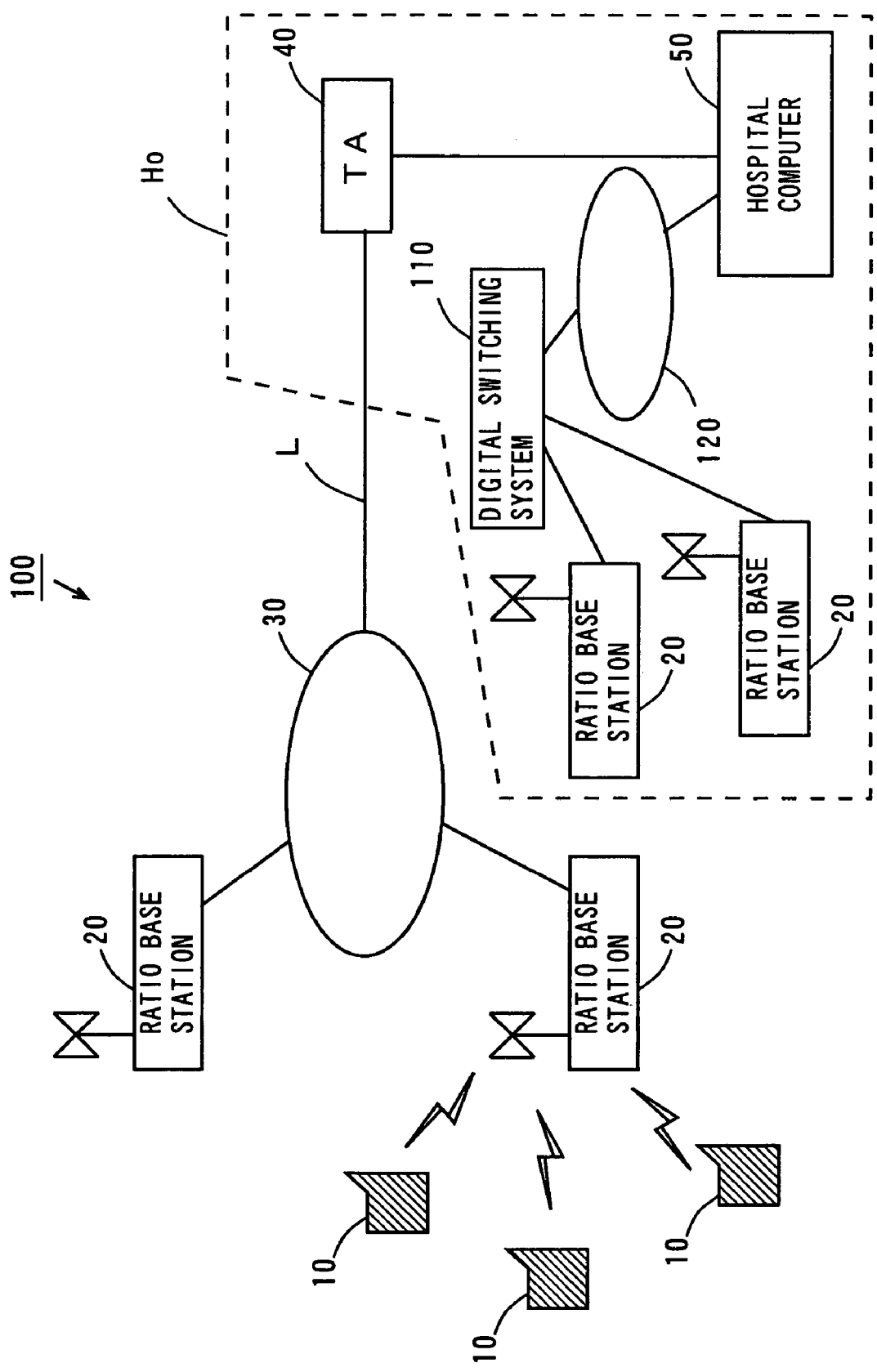
FIG. 2 is a block diagram showing the structure of the electrocardiogram monitoring system using the portable electrocardiograph according to the first embodiment.

FIG. 2 is a block diagram showing the structure of the electrocardiogram monitoring system using the portable electrocardiograph according to the first embodiment.

As shown in FIG. 2, an electrocardiogram monitoring system 100 comprises portable electrocardiographs 10, a plurality of radio base stations 20, a public network 30, a TA (Terminal Adapter) 40, a hospital computer 50, a line L, a digital switching system 110, and a private network 120. The line L is, for example, an IDSN (Integrated Services Digital Network) line. In the hospital Ho, the plurality of base stations 20, TA 40, hospital computer 50, digital switching system 110, and private network 120 are provided.

The electrocardiogram data and acceleration data obtained by the portable electrocardiograph 10 of each patient outside the hospital Ho are transmitted to the radio base station 20, and transmitted from the radio base station 20 via the public network 30, line L, and TA 40 to the hospital computer 50. The electrocardiograms and accelerations of the plurality of patients Y are displayed on the screen of the hospital computer 50 in real time based on the electrocardiogram data and acceleration data.

In the case where a patient carries out therapeutic exercise inside the hospital Ho, the electrocardiogram data and acceleration data obtained by the portable electrocardiograph 10 of the patient are transmitted to the radio base station 20 in the hospital Ho, and transmitted from the radio base station 20 via the digital switching system 110 and private network 120 to the hospital computer 50. The electrocardiograms and accelerations of a plurality of patients are displayed on the screen of the hospital computer 50 in real time based on the electrocardiogram data and acceleration data.

The diagnostician thus makes a diagnosis while performing real time and centralized monitoring of the electrocardiograms and accelerations of the plurality of patients which are displayed on the screen of the hospital computer 50. In the case where any of the patients is in bad condition, the diagnostician transmits an alarm signal via the TA 40, line L, public network 30, and radio base station 20 to the portable electrocardiograph 10 of the patient outside the hospital Ho by operating the hospital computer 50, so that he/she can immediately stop the patient's exercise. Alternatively, the diagnostician transmits an alarm signal via the private network 120, digital switching system 110, and radio base station 20 to the portable electrocardiograph 10 of the patient inside the hospital Ho by operating the hospital computer 50, so that he/she can stop the patient's exercise.

Figure 3:
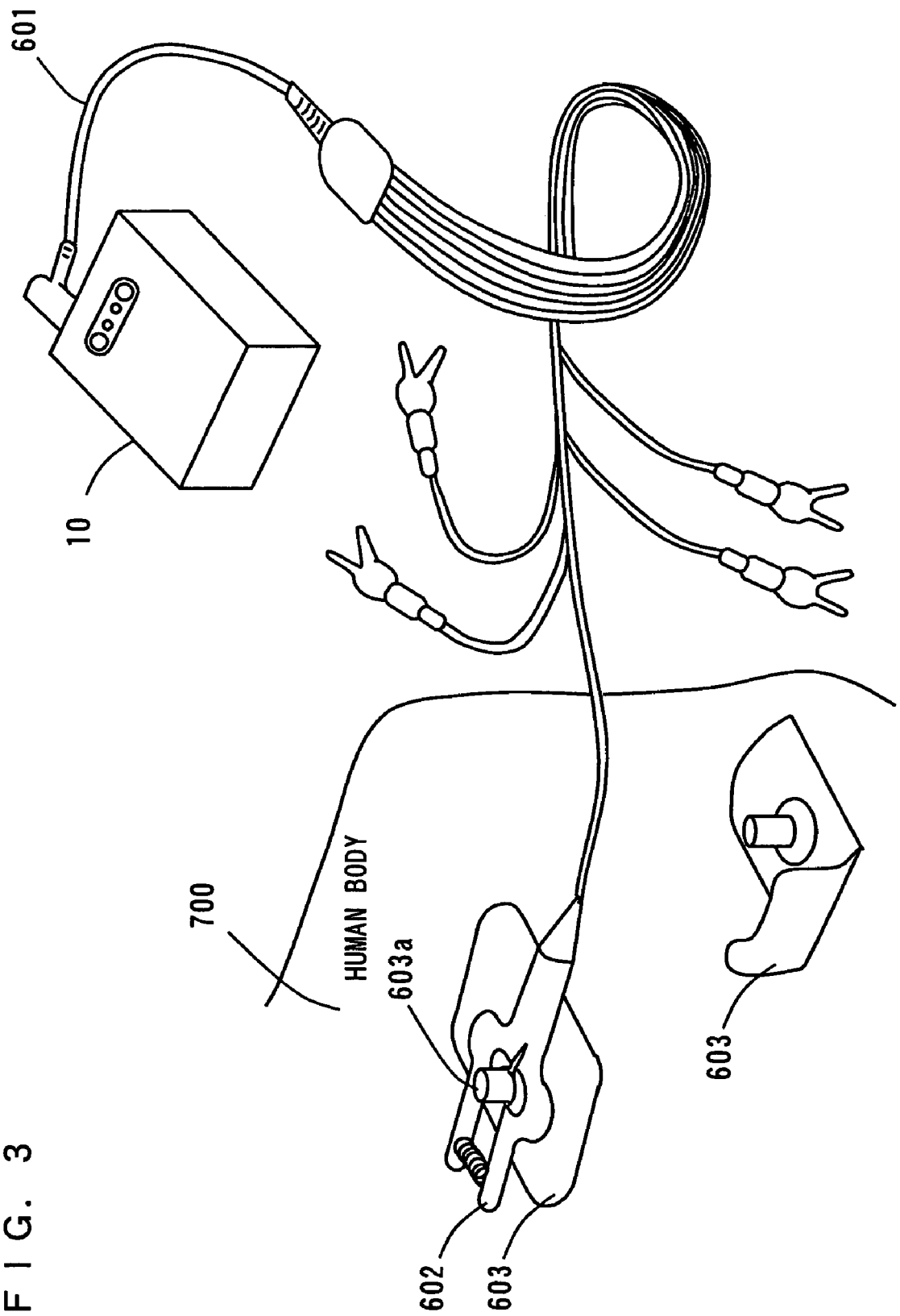
FIG. 3 is a schematic view showing the appearance of the portable electrocardiograph used in the electrocardiogram monitoring system according to the first embodiment and how the portable electrocardiograph is attached to a human body.

FIG. 3 is a schematic view showing the appearance of the portable electrocardiograph used in the electrocardiogram monitoring system according to the first embodiment and how the portable electrocardiograph is attached to a human body.

As shown in FIG. 3, a cable 601 is connected to the portable electrocardiograph 10, and a clamp electrode 602 is connected to the end of the cable 601. In the attachment of the portable electrocardiograph 10 to a human body 700, a disposable electrode 603 is first fixed onto the human body 700. The disposable electrode 603 is provided with a terminal 603a, which is inserted into the clamp electrode 602. The portable electrocardiograph 10 can thus measure a faint potential difference (voltage) by the stimulation process of the heart muscle of the human body 700 as an electrocardiogram.

Figure 4:
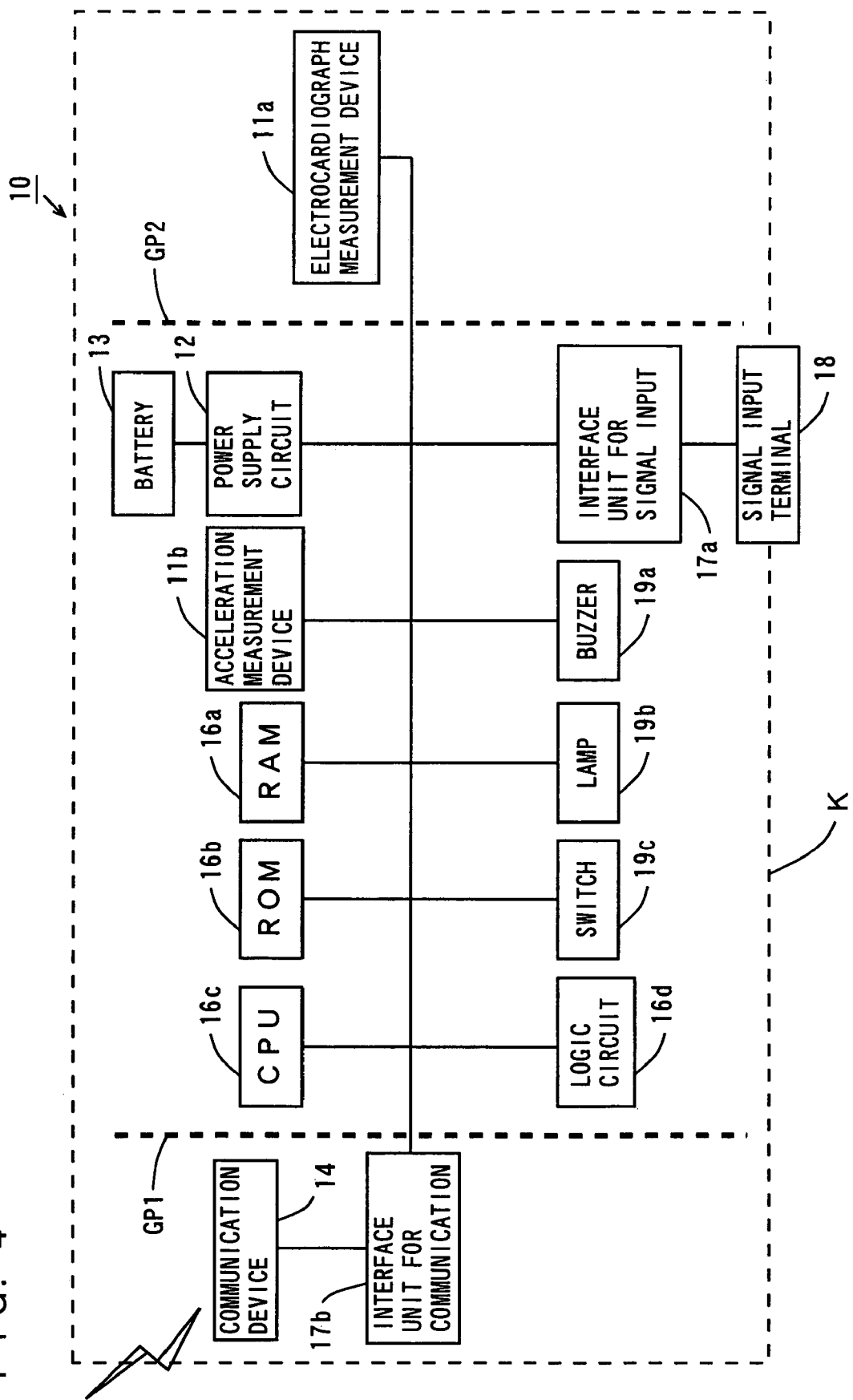
FIG. 4 is a block diagram showing one example of the structure of the portable electrocardiograph according to the first embodiment.

FIG. 4 is a block diagram showing one example of the structure of the portable electrocardiograph according to the first embodiment. In the following description, "electrocardiogram signal" represents an analog signal of the electrocardiogram produced by an electrocardiogram measurement device described later based on the faint voltage obtained by the disposable electrode 603 shown in FIG. 3 that is attached to the human body, whereas "acceleration signal" represents an analog signal of the acceleration measured by an acceleration measurement device described later. In addition, "electrocardiogram data" represents digital data formed based on the electrocardiogram signal, whereas "acceleration data" represents digital data formed based on the acceleration signal.

In FIG. 4, the portable electrocardiograph 10 includes an electrocardiogram measurement device 11a, an acceleration measurement device 11b, a power supply circuit 12, a battery 13, a CPU (Central Processing Unit) 16c, a ROM (Read Only Memory) 16b, a RAM 16a, a logic circuit 16d, an interface 17a for signal input, a signal input terminal 18, a communication device 14, an interface 17b for communication, a buzzer 19a, a lamp 19b, a switch 19c, ground planes GP1, GP2, and a casing K.

The communication device 14 and interface unit 17b for communication are separated from the other components by the ground plane GP1, and the electrocardiogram measurement device 11a is separated from the other components by the ground plane GP2. Accordingly, the two ground planes GP1, GP2 are provided between the communication device 14 and the interface unit 17b for communication and the electrocardiogram measurement device 11a. This structure will be described later in detail.

The interface unit 17b for communication is connected to the communication device 14, connecting the CPU 16c and the communication device 14 with each other. The communication device 14 is connectable to the radio base station 20 shown in FIG. 2 by radio communication. In the present embodiment, the communication device 14 is a PHS (Personal Handyphone System).

A system program is stored in the ROM 16b. In the RAM 16a, electrocardiogram data, acceleration data, and so on as described later are stored. The CPU 16c executes the system program stored in the ROM 16b on the RAM 16a. The logic circuit 16d includes an analog-digital converter, a ring-buffer, and so on, and has its operation controlled by the CPU 16.

The power supply circuit 12 connects the battery 13 and the other components inside the portable electrocardiograph 10 with each other to supply the electricity in the battery 13 to each component. The interface unit 17a for signal input connects the signal input terminal 18 and the CPU 16c, the RAM 16a, and the logic circuit 16d.

The switch 19c is connected to the CPU 16c to supply a given command signal to the CPU 16c based on the operation of a user. The lamp 19b and buzzer 19a are connected to the CPU 16c, respectively, and have their operations controlled by the CPU 16c.

The electrocardiogram measurement device 11a is connected to the signal input terminal 18 via the interface 17a for signal input to produce an electrocardiogram signal based on the faint voltage detected in the human body 700 to supply the produced electrocardiogram signal to the logic circuit 16d, and so on. The acceleration measurement device 11b measures the acceleration of the main body of the portable electrocardiograph 10, and supplies the measurement result as acceleration data to the logic circuit 16d, RAM 16a, and so on. Note that the acceleration measurement device 11b contains an analog-digital converter.

The casing K covers all of the components in the portable electrocardiograph 10. Here, inside the casing K, the two ground planes GP1, GP2 are found as mentioned before. This divides the inside of the casing K into three spaces.

The inner operation of the portable electrocardiograph 10 will be then described. In the use of the portable electrocardiograph 10, a faint voltage by the stimulation process of the heart muscle of the human body 700 is input to the signal input terminal 18 via the disposable electrode 603, clamp electrode 602, and cable 601 shown in FIG. 3. The faint voltage input to the signal input terminal 18 is then input to the electrocardiogram measurement device 11a via the interface unit 17a for signal input.

The electrocardiogram measurement device 11a supplies an electrocardiogram signal based on the input faint voltage to the logic circuit 16d. In the logic circuit 16d, the input electrocardiogram signal is analog-digital converted by the analog-digital converter contained therein, and electrocardiogram data is produced. The produced electrocardiogram data is subsequently transmitted to the RAM 16a.

Meanwhile, the acceleration measurement device 11b measures the acceleration of the main body of the portable electrocardiograph 10. The acceleration measurement device 11b produces an acceleration signal in analog form based on the measured acceleration. The input acceleration signal is analog-digital converted by the analog-to-digital converter contained in the acceleration measurement device 11b, and acceleration data is produced. The produced acceleration data is subsequently transmitted to the RAM 16a. The RAM 16a stores the input electrocardiogram data and acceleration data. It is desirable that the RAM 16a is capable of storing the electrocardiogram data and acceleration data of not less than 24 hours.

The electrocardiogram data and acceleration data are transmitted via the ring-buffer in the logic circuit 16d, interface unit 17b for communication, and communication device 14 to the hospital computer 50 shown in FIG. 3 based on the operation of the CPU 16c.

Referring now to FIGS. 5-8, the arrangement and structure of each of the components in the portable electrocardiograph 10 according to the first embodiment will be described in detail.

Figure 6:
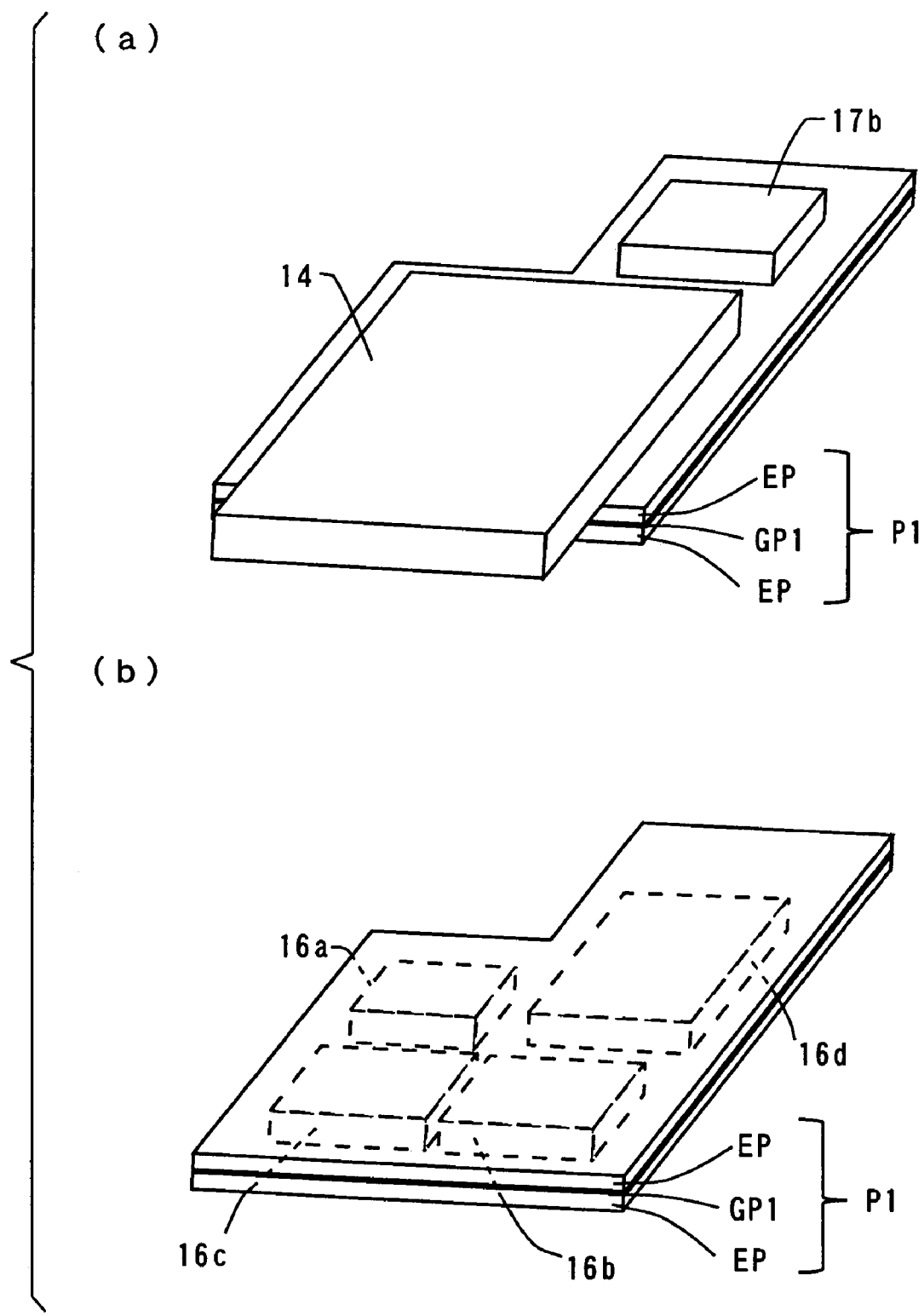
FIG. 6 is a schematic view showing the mounted state of each of the components provided in a first multi-layered circuit board shown in FIG. 5.
Figure 7:
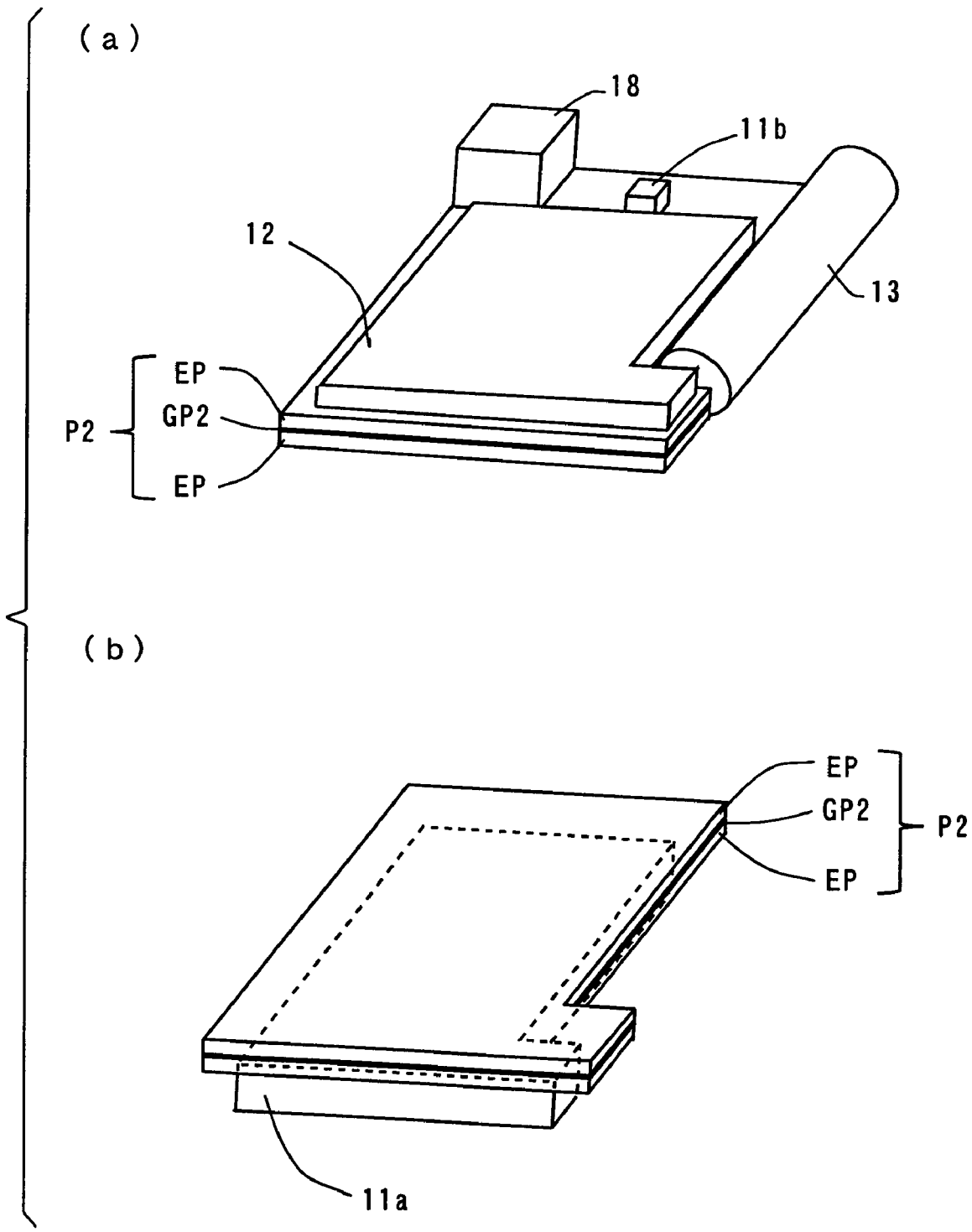
FIG. 7 is a schematic view showing the mounted state of each of the components provided in a second multi-layered circuit board shown in FIG. 5.
Figure 8:
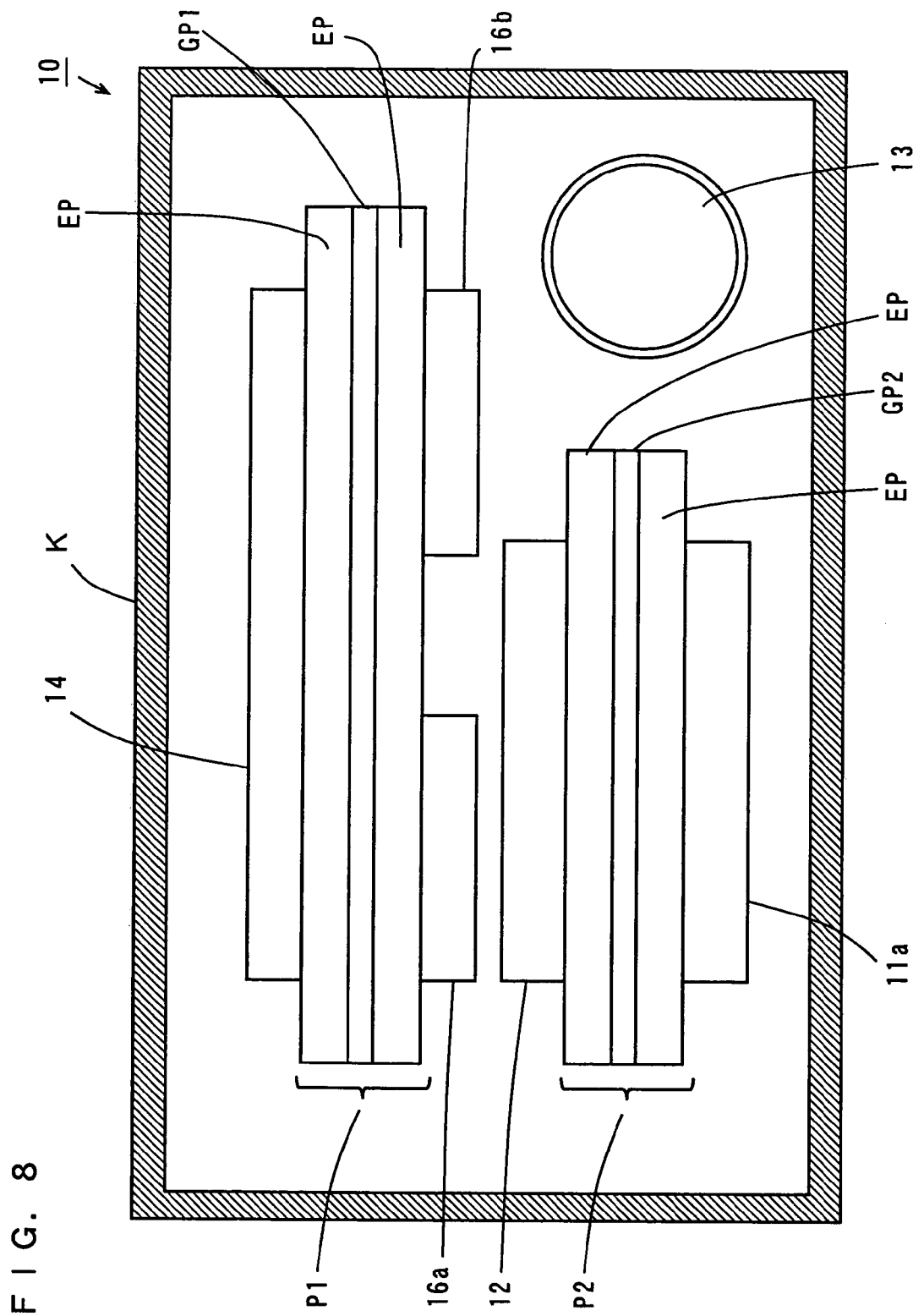
FIG. 8 is an X-X line cross-sectional view of the portable electrocardiograph shown in FIG. 5.

FIG. 5 is a schematic perspective view showing one example of the inner structure of the portable electrocardiograph according to the first embodiment. FIG. 6 is a schematic view showing the mounted state of each of the components provided in a first multi-layered circuit board shown in FIG. 5. FIG. 7 is a schematic view showing the mounted stated of each of the components provided in a second multi-layered board shown in FIG. 5. FIG. 8 is an X-X line cross-sectional view of the portable electrocardiograph shown in FIG. 5.

Referring to FIGS. 5 and 6(a), the communication device 14 and interface unit 17b for communication are mounted on the upper surface of the first multi-layered circuit board P1. Referring to FIGS. 5 and 6(b), the CPU 16c, ROM 16b, RAM 16a, and logic circuit 16d are mounted on the lower surface of the first multi-layered circuit board P1. Here, the first multi-layered circuit board P1 has the ground plane GP1 made of copper or the like between circuit board layers EP, each made of a glass epoxy resin or the like. Note that the ground terminals of the communication device 14 and each of the other components are connected to the ground plane GP1.

Referring to FIGS. 5 and 7(a), the signal input terminal 18, acceleration measurement device 11b, and power supply circuit 12 are mounted on the upper surface of a second multi-layered circuit board P2. The power supply circuit 12 is connected to the battery 13 loaded into a notch portion of the second multi-layered circuit board P2. In addition, it is seen from FIGS. 5 and 7(a) that the electrocardiogram measurement device 11a is mounted on the lower surface of the second multi-layered circuit board P2. Here, the second multi-layered circuit board P2 has the ground plane GP2 made of copper or the like between circuit board layers EP, each made of a glass epoxy resin or the like as shown in FIG. 7. Note that the ground terminals of the electrocardiogram measurement device 11a, acceleration measurement device 11b, and each of the other components are connected to the ground plane GP2.

Referring to the X-X line cross-sectional view of FIG. 5 shown in FIG. 8, the space inside of the casing K is divided into three spaces, i.e., an upper space, a central space, and a lower space, by the first multi-layered circuit board P1 and second multi-layered circuit board P2. The electrocardiogram measurement device 11a is located in the lower space inside the casing K, and the communication device 14 is located in the upper space inside the casing K. As mentioned above, the ground planes GP1, GP2 are provided inside the first multi-layered circuit board P1 and second multi-layered circuit board P2, respectively.

As for the PHS used as the communication device 14, it emits radio waves of a 1.9 GHz band with a power of approximately 10 mW. Meanwhile, the electrocardiogram measurement device 11a measures a faint voltage of 1-10 mV generated in the human body 700. Therefore, in the case where the electrocardiogram measurement device 11a receives the radio waves emitted by the PHS in measuring electrocardiogram, a high-frequency noise is caused in the measurement result, which prevents the acquisition of an accurate electrocardiogram.

In the portable electrocardiograph 10 according to the present embodiment, the ground planes GP1, GP2 are provided between the communication device 14 and the electrocardiogram measurement device 11a as mentioned above so that the communication device 14 and electrocardiogram measurement device 11a are isolated from each other, and therefore, the radio waves emitted from the communication device 14 are prevented from reaching the electrocardiogram measurement device 11a. This enables the electrocardiogram measurement device 11a to accurately measure an electrocardiogram based on the faint voltage generated in the human body 700 without being affected by the radio waves emitted from the communication device 14. In addition, the communication device 14 and electrocardiogram measurement device 11a are integrally housed inside the casing K, leading to smaller size and further portability of the portable electrocardiograph 10.

The size of the portable electrocardiograph 10 according to the present embodiment is, for example, approximately 9 cm in length, 6 cm in width, and 2.5 cm in thickness. The size of the portable electrocardiograph 10 is not limited thereto, and may desirably be made smaller to the extent that the electrocardiogram measurement device 11a can accurately measure the electrocardiogram without being affected by the radio wave emission of the communication device 14.

In the portable electrocardiograph 10 according to the present embodiment, the electrocardiogram and acceleration can be accurately measured by the electrocardiogram measurement device 11a and acceleration measurement device 11b, while the electrocardiogram data and acceleration data can be transmitted to the hospital computer 50 shown in FIG. 2 in real time by the communication device 14. As a result, the diagnostician can monitor the electrocardiogram and acceleration of a patient outside the hospital in real time.

While in the present embodiment, the two ground planes GP1, GP2 are provided between the electrocardiogram measurement device 11a and the communication device 14, the number of the ground planes is not limited thereto, and it may be one or not less than three, as long as the radio waves emitted by the communication device 14 can be prevented from affecting the electrocardiogram measurement device 11a. For example, the electrocardiogram measurement device 11a may be mounted on one side of one multi-layered circuit board including one ground plane, and the communication device 14 may be mounted on the other side thereof.

Furthermore, in the present embodiment, the electrocardiogram data and acceleration data are stored in the RAM 16a. Therefore, even in the case where the electrocardiogram data and acceleration data obtained by the electrocardiogram measurement device 11a and acceleration measurement device 11b are not normally radio-transmitted, with the accurate electrocardiogram data and acceleration data stored in the RAM 16a, the patient can receive an accurate diagnosis after the measurements of the electrocardiogram and acceleration by submitting to the diagnostician the RAM 16a in which the electrocardiogram data and acceleration data are stored.

FIG. 9 is a block diagram showing the structure of a hospital computer in the electrocardiogram monitoring system using the portable electrocardiograph according to the first embodiment.

As shown in FIG. 9, the hospital computer 50 includes a CPU 501, a RAM 502, a ROM 503, an external storage 504, a recording medium drive 505, an interface unit 506, and a display device 507.

The interface unit 506 is connected to the TA 40, connecting the CPU 501 and the TA 40 with each other. In addition, the TA 40 is connected to the public network 30 via the line L.

A system program is stored in the ROM 503. The recording medium drive 505 comprises a CD (Compact Disc) drive, or a floppy disc drive, for example, and performs reading and writing of data with respect to a recording medium 508, which is a CD, or a floppy disc, for example. An electrocardiogram monitoring program is recorded in the recording medium 508. The external storage 504 comprises a hard disc, for example, and stores the electrocardiogram monitoring program read by the recording medium 508 via the recording medium drive 505. The CPU 501 executes the electrocardiogram monitoring program stored in the external storage 504 on the RAM 502. The display device 507 comprises a CRT (Cathode Ray Tube), a plasma display, or a liquid display, for example, and displays various pieces of information on the electrocardiogram.

Various types of recording mediums can be used as the recording medium 508 that records the electrocardiogram monitoring program, for example, semiconductor memories such as a ROM, or a hard disc. Alternatively, the electrocardiogram monitoring program may be downloaded into the external storage 504 via the transmission medium such as the TA 40 and line L, and be executed on the RAM 502.

The processing carried out for the electrocardiogram data and acceleration data by the hospital computer 50 shown in FIG. 2 will be then described.

As mentioned above, the electrocardiogram data and acceleration data are input to the hospital computer 50 by the portable electrocardiograph 10. The hospital computer 50 forms the following data based on the input electrocardiogram data.

Figure 10:
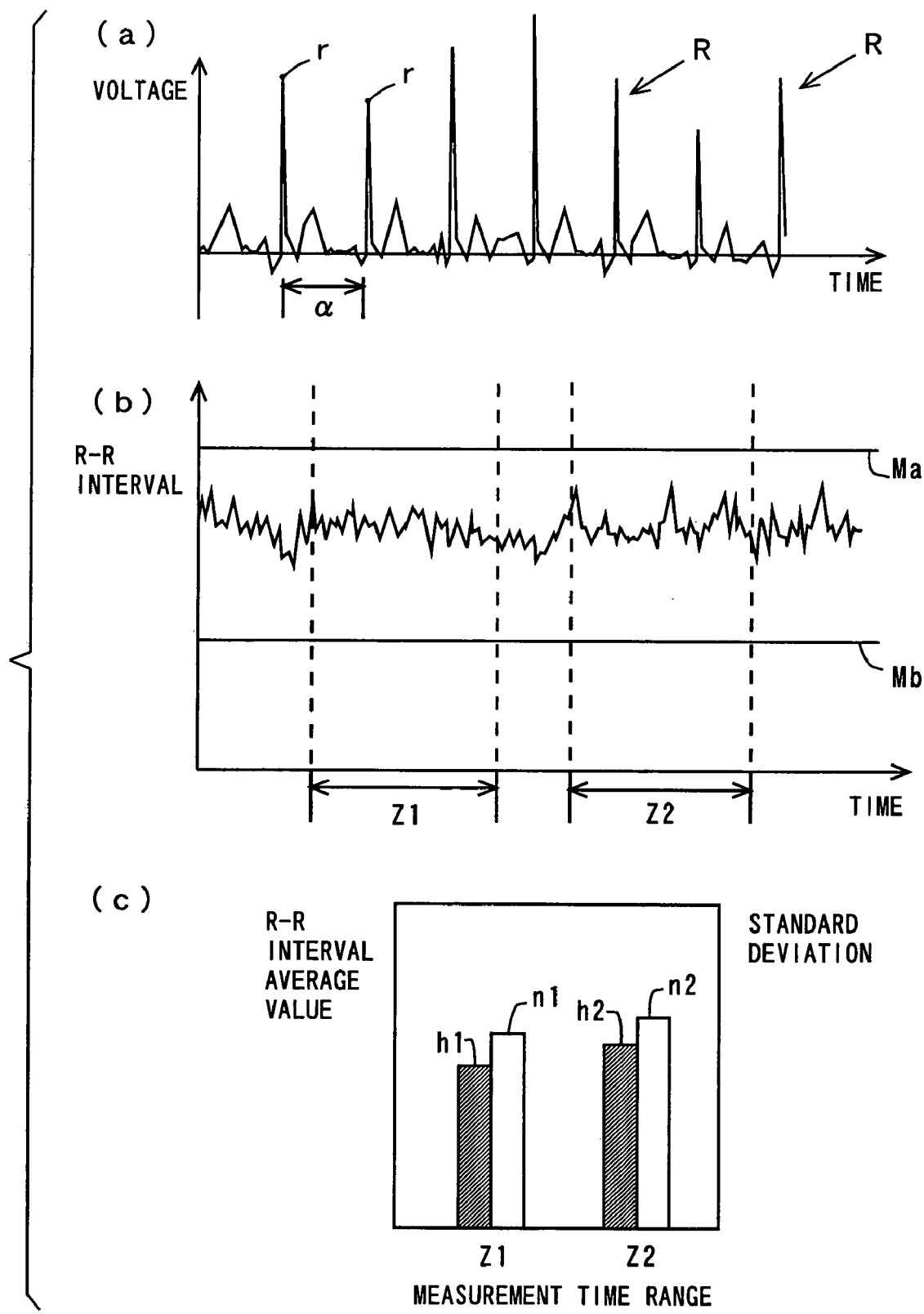
FIG. 10 is a schematic view showing one example of the data formed by the hospital computer based on the input electrocardiogram.

FIG. 10 is a schematic view showing one example of the data formed by a hospital computer based on the input electrocardiogram.

As shown in FIG. 10 (a), the hospital computer 50 forms electrocardiogram waveform data based on the electrocardiogram data transmitted by the portable electrocardiograph 10. In FIG. 10 (a), the ordinate represents a faint voltage generated in the human body 700, whereas the abscissa represents time. On the electrocardiogram waveform data herein, R waves, each representing the stimulation process of the ventricular muscle, are generated at a floating cycle.

The hospital computer 50 extracts the maximum value of each of the R waves based on the formed electrocardiogram waveform data. In FIG. 10 (a), the maximum voltage of each of the R waves is extracted as a maximum value r. Moreover, while extracting the maximum value of the R wave, the hospital computer 50 also calculates a time interval $\alpha$ between adjacent R waves from the difference between the measurement times of the maximum voltages in the respective R waves. The time interval $\alpha$ between the adjacent R waves is hereinafter referred to as an R-R interval. The heart rate of a patient to be measured is calculated from the R-R interval.

The hospital computer 50 subsequently forms pulsation waveform data, which represents the relationship between the R-R interval and time. FIG. 10 (b) shows one example of the pulsation waveform data representing the relationship between the R-R interval and time.

With the pulsation waveform data, the movement of the heart of the patient, whether arrhythmia is occurring, for example, can be monitored in real time. In addition, by setting an upper limit value Ma and a lower limit value Mb of the R-R interval on the pulsation waveform data, the abnormal condition of the patient to be measured, for example, can be more readily found. It is preferable that the upper limit value Ma and lower limit value Mb can be set depending on the patient.

The hospital computer 50 may also calculate an average value and a standard deviation in the R-R interval at a particular measurement time based on the pulsation waveform data. In this case, as shown in FIG. 10(b), the hospital computer 50 calculates the data of the average values and the data of the standard deviations to the total measurement time in the R-R intervals in respective measurement time ranges Z1, Z2 arbitrarily designated by the diagnostician.

FIG. 10 (c) shows one example of data of the average values and data of the standard deviations to the total measurement time in the R-R intervals in the respective measurement time ranges Z1, Z2 designated in FIG. 10 (b). Referring to FIG. 10 (c), the bar graph h1 represents the average value in the R-R interval in the measurement time range Z1, and the bar graph n1 represents the standard deviation, whereas the bar graph h2 represents the average value in the R-R interval in the measurement time range Z2, and the bar graph n2 represents the standard deviation.

Moreover, the hospital computer 50 stores the input acceleration data while processing the electrocardiogram data.

In the hospital computer 50 according to the present embodiment, information on each of a plurality of patients, such as name, age, or disease condition is recorded in advance. The hospital computer 50 accordingly displays on the display device 507 the electrocardiogram waveform data, pulsation waveform data, and acceleration data of a patient with his/her information.

The hospital computer 50 performs the above-described operations in real time for the electrocardiogram data and acceleration data transmitted via the public network 30 shown in FIG. 2 from the portable electrocardiograph 10.

The displayed contents of the hospital computer 50 according to the present embodiment will be now described.

Figure 11:
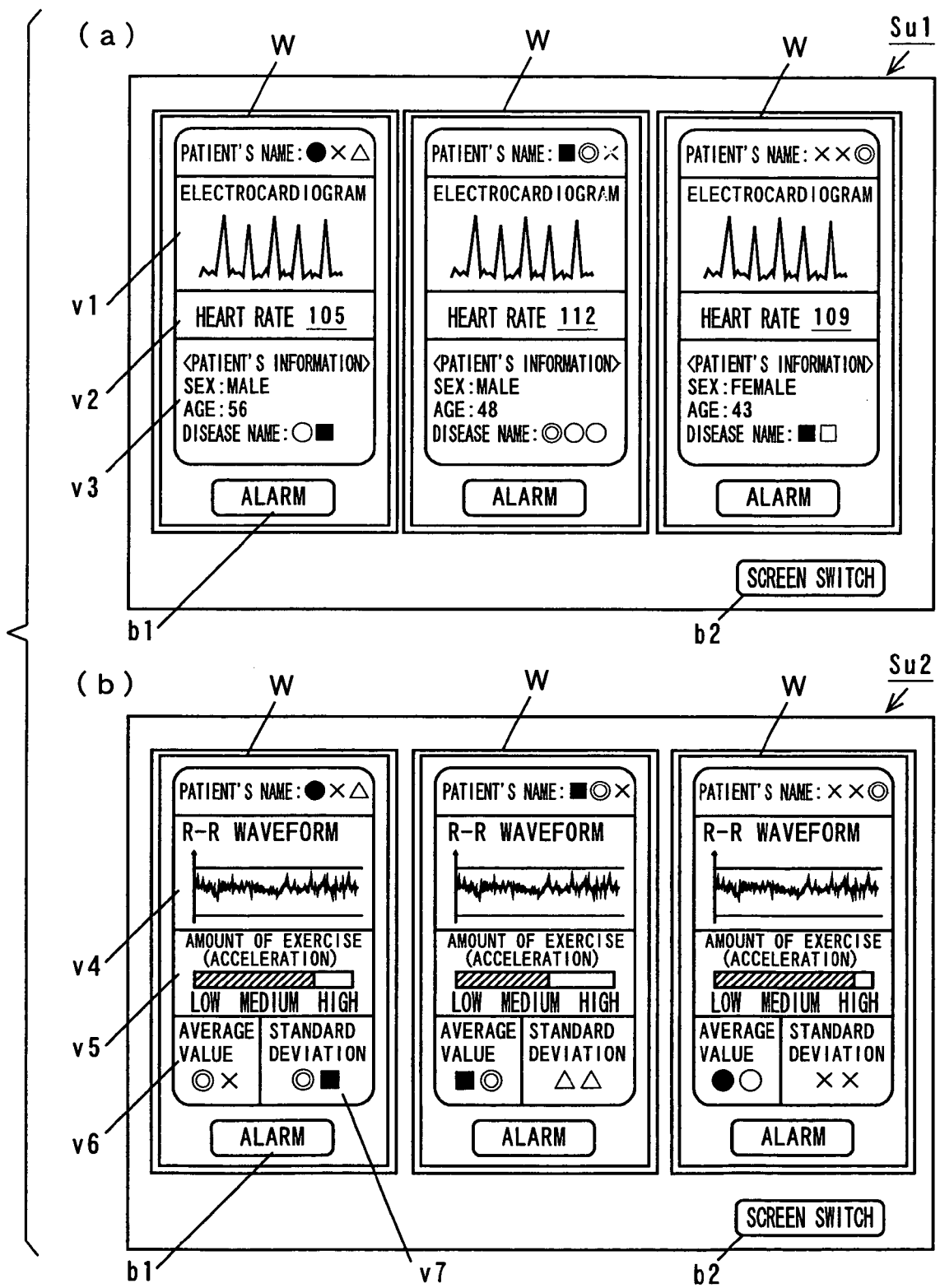
FIG. 11 is a schematic view showing one example of the screen of the hospital computer presenting a diagnostician with the condition of the measurement of the electrocardiogram of a patient.

FIG. 11 is a schematic view showing one example of the screen of a hospital computer presenting the diagnostician with the condition of the measurement of the electrocardiogram of a patient. FIG. 11 (a) shows a first display screen Su1, whereas FIG. 8 (b) shows a second display screen Su2.

Referring to FIG. 11 (a), a plurality of windows W for the respective patients currently being measured and a screen switching button b2 are displayed on the first display screen Su1. Inside each of the windows W, an electrocardiogram waveform v1, a heart rate v2, patient information v3, and an alarm button b1 are displayed.

Referring to FIG. 11 (b), a plurality of windows W for the respective patients being measured and a screen switching button b2 are displayed on the second display screen Su2. Inside the window W, a pulsation waveform diagram v4, an amount v5 of the exercise currently being performed, an average value v6 in the R-R interval, a standard deviation v7 in the R-R interval, and an alarm button b1 are displayed.

The electrocardiogram waveform v1, heart rate v2, patient information v3, pulsation waveform diagram v4, amount v5 of the exercise currently being performed, average value v6 in the R-R interval, standard deviation v7 of the R-R interval are displayed based on the aforementioned electrocardiogram waveform data, pulsation waveform data, and acceleration data.

The display switching button b2 is used when the diagnostician switches the screen displayed on the display device 507 "from the first display screen Su1 to the second display screen Su2" or "from the second display screen Su2 to the first display screen Su1".

The alarm button b1 is used when the diagnostician determines that "the patient is in dangerous condition or abnormal condition" from the information obtained on the first display screen Su1 and second display screen Su2.

For example, the diagnostician clicks the alarm button b1 when he/she determines that "the patient is in dangerous condition or abnormal condition". This causes the hospital computer 50 to transmit an alarm signal that commands a "buzzer on" or "lamp on" to the portable electrocardiograph 10 of the target patient. The portable electrocardiograph 10 is thus allowed to make the patient be aware of his/her abnormal condition with the buzzer 19a or lamp 19b.

Lastly, the operation procedures of the electrocardiogram monitoring system, processing operation of the portable electrocardiograph 10, and processing operation of the hospital computer 50 according to the present embodiment will be described, referring to FIGS. 9 to 12.

Figure 12:
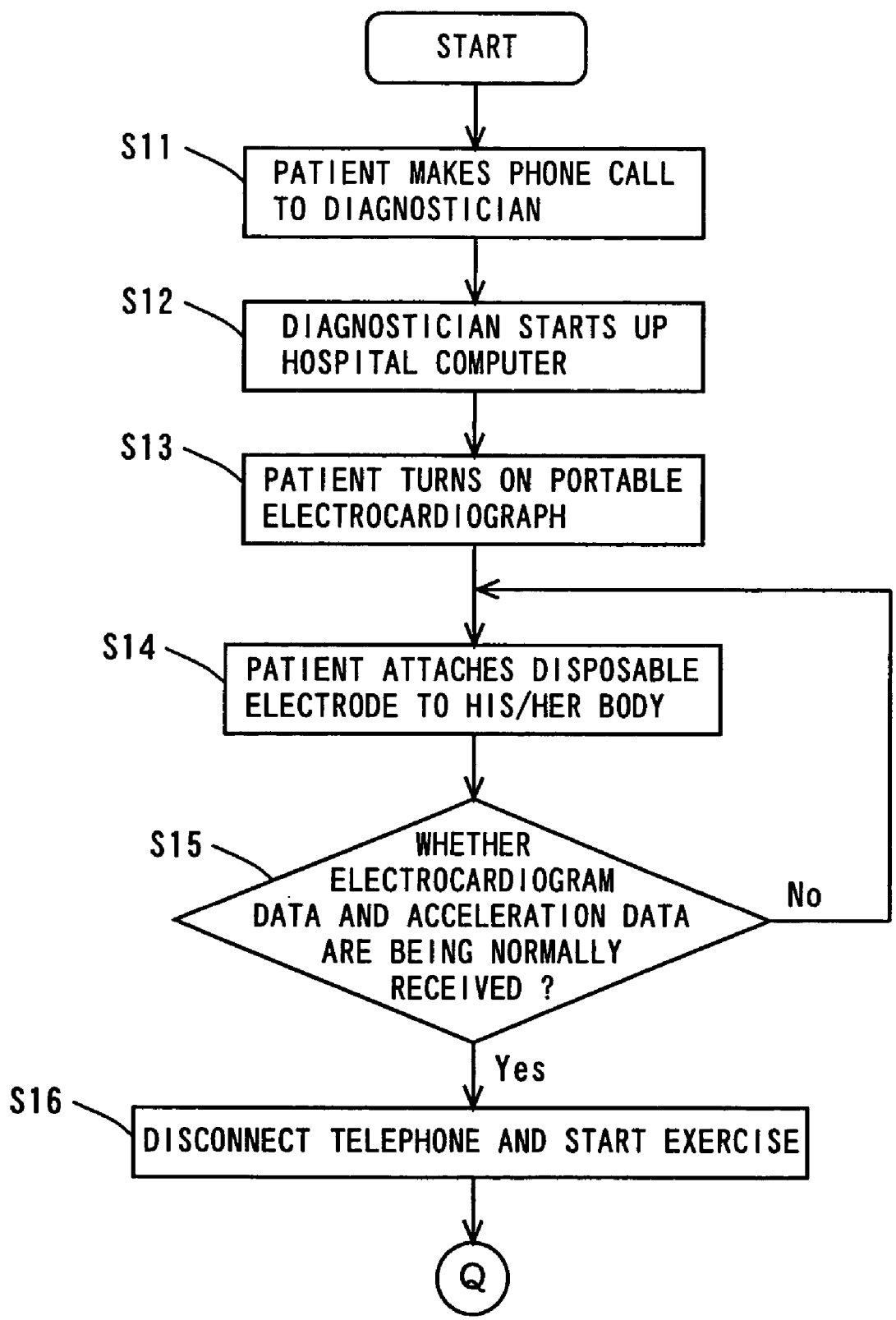
FIG. 12 is a flow chart showing the operation procedures of the electrocardiogram monitoring system according to the first embodiment.
Figure 13:
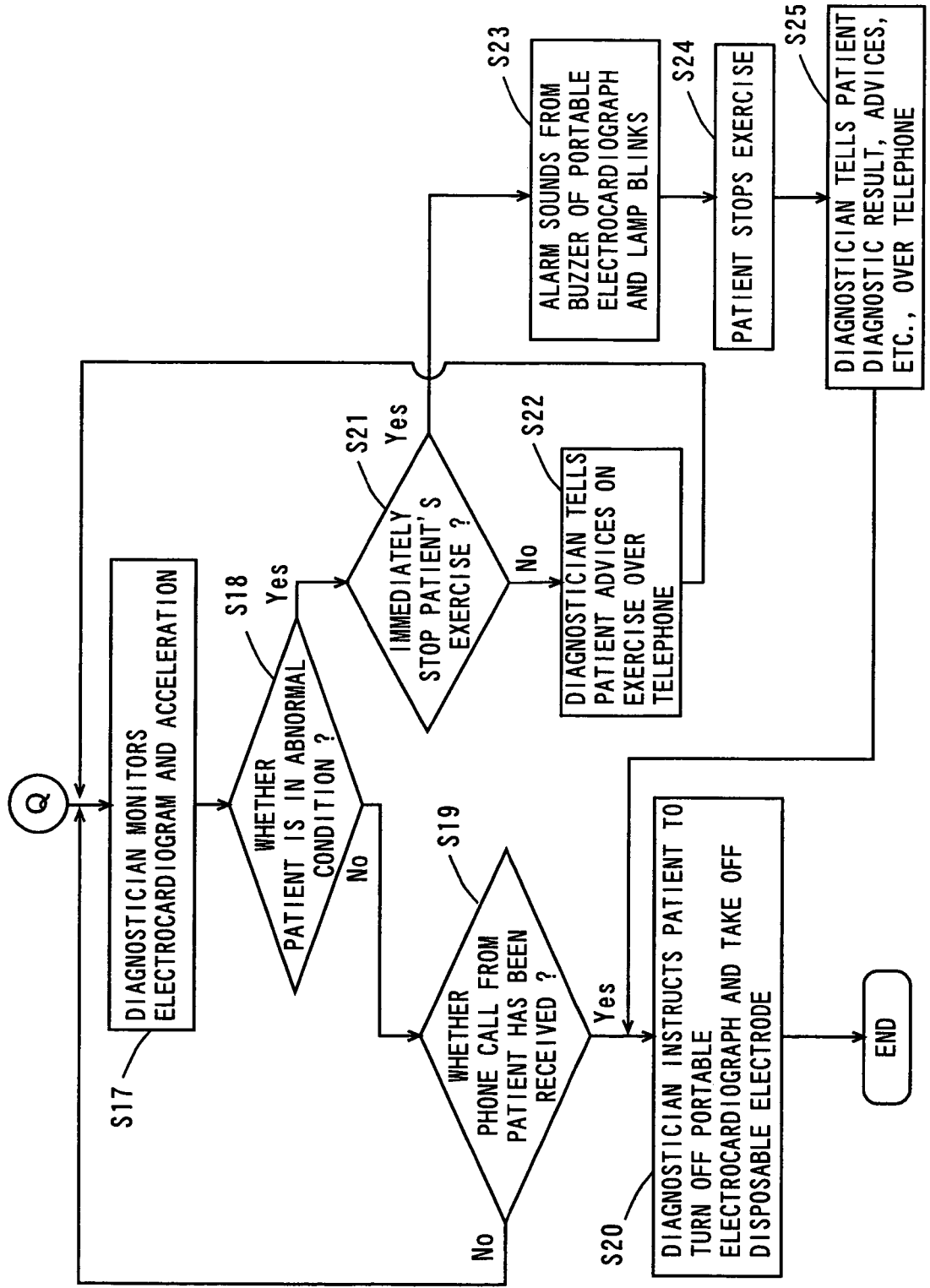
FIG. 13 is a flow chart showing the operation procedures of the electrocardiogram monitoring system according to the first embodiment.

FIGS. 12 and 13 are flow charts respectively showing the operation procedures of the electrocardiogram monitoring system according to the first embodiment.

First, a patient informs in advance the diagnostician over the telephone that he/she will start the therapeutic exercise (Step S11). The diagnostician in the hospital then starts up the hospital computer 50 after receiving the phone call from the patient (Step S12). The patient turns on the portable electrocardiograph 10 of his/her own after confirming that the diagnostician in the hospital has started up the hospital computer 50 (Step S13).

The patient then attaches the disposable electrode 603 to his/her body (Step S14). This causes the portable electrocardiograph 10 to radio-transmit the electrocardiogram data and acceleration data.

The diagnostician determines whether the electrocardiogram data and acceleration data radio-transmitted by the portable electrocardiograph 10 are normally being received by confirming the displayed contents of the hospital computer 50 (Step S15).

In the case where the diagnostician determines that the electrocardiogram data and acceleration data are not normally being received from the portable electrocardiograph 10, he/she instructs the patient to see if the disposable electrode is attached properly. The patient thus re-attaches the disposable electrode 603 to his/her body (Step S14).

At Step S15, once the diagnostician determines that the electrocardiogram data and acceleration data are normally being received from the portable electrocardiograph 10, he/she tells the patient to disconnect the telephone and start the exercise (Step S16).

Meanwhile, the diagnostician monitors the electrocardiogram and acceleration of the patient displayed on the hospital computer 50 (Step S17) to determine whether the patient is in abnormal condition (Step S18).

Here, in the case where the diagnostician determines that the patient is in normal condition, he/she continues monitoring the electrocardiogram and acceleration back to Step S17 until he/she is informed from the patient over the telephone that the patient has finished exercise.

After being informed that the patient has completed the exercise, the diagnostician instructs him/her to turn off the portable electrocardiograph 10, and take off the disposable electrode 603 (Step S20). The therapeutic exercise of the patient is thus completed.

On the other hand, in the case where the diagnostician determines that the patient is in abnormal condition at Step S18, he/she determines whether the patient should immediately stop the exercise due to the abnormal condition (Step S21).

Once the diagnostician determines that the patient does not have to immediately stop the exercise, he/she advises the patient over the telephone, for example, to lighten the exercise (Step S22). The diagnostician then again repeats the operation of Step S17.

In the case where the diagnostician determines that the patient must immediately stop the exercise, he/she transmits an alarm signal to the portable electrocardiograph 10 of the patient for the output of an alarm. This causes the buzzer 19a of the portable electrocardiograph 10 to sound an alarm, and the lamp 19b thereof to blink in red, which is indicative of an alarm (Step S23). The patient confirms the alarm sound from the buzzer 19a and the blink of the lamp 19b from the portable electrocardiograph 10 of his/her own, and stops the exercise (Step S24). After that, the diagnostician tells the patient the diagnostic result of the monitoring, advices on the exercise method, etc., over the telephone (Step S25), and performs the operation of Step S20.

Figure 14:
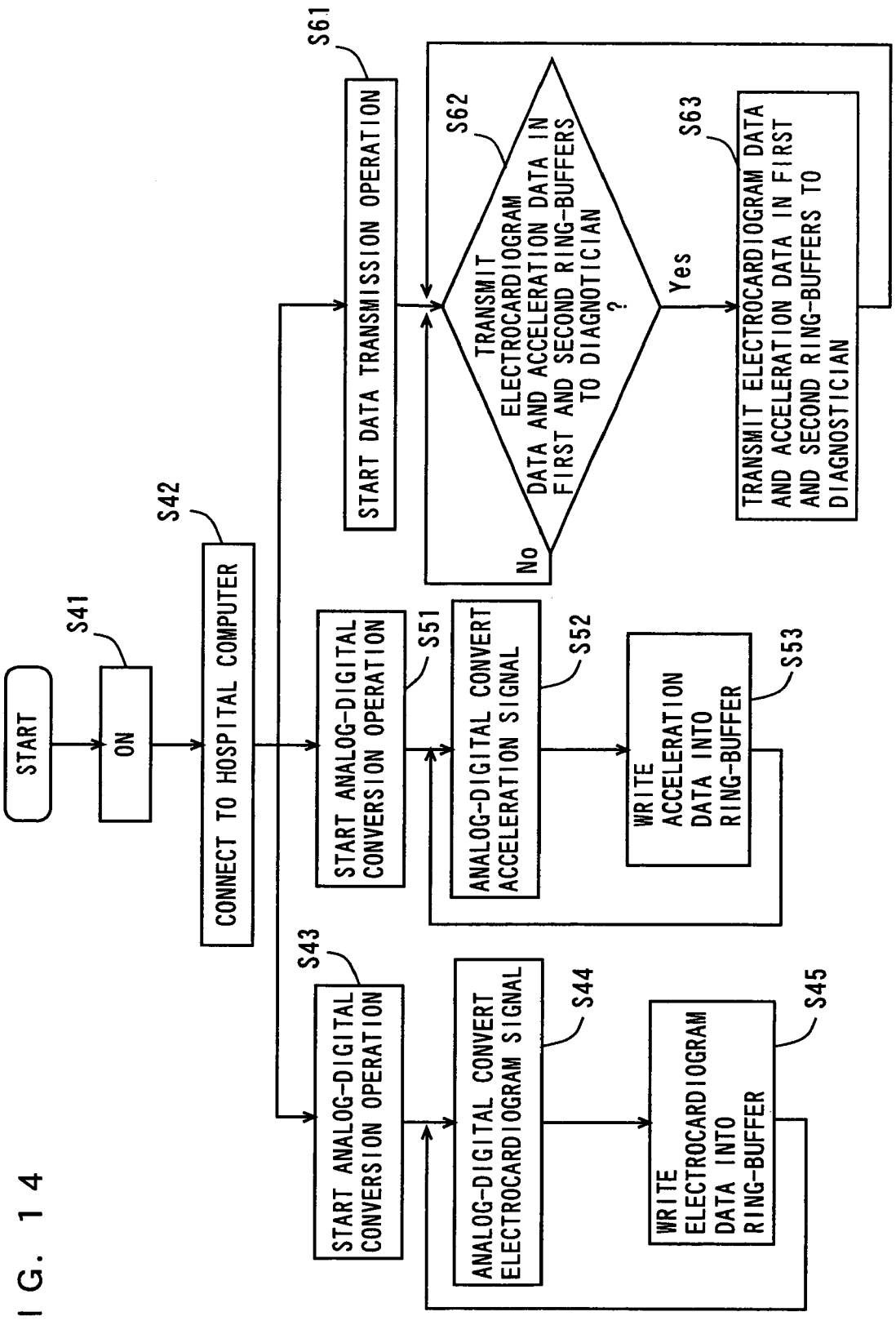
FIG. 14 is a flow chart showing the processing operation of the portable electrocardiograph according to the first embodiment.

FIG. 14 is a flow chart showing the processing operation of the portable electrocardiograph 10 according to the first embodiment. Here, the logic circuit 16d includes a first ring-buffer that temporarily stores the electrocardiogram data and a second ring-buffer that temporarily stores the acceleration data.

First, the portable electrocardiograph 10 is turned on (Step S41). The communication device 14 in the portable electrocardiograph 10 is then connected to the hospital computer 50 (Step S42). This causes the following three processings to be simultaneously performed.

At a first processing, the CPU 16c instructs the analog-digital converter in the logic circuit 16d to start conversion operation (Step S43). The analog-digital converter in the logic circuit 16d accordingly analog-digital converts the electrocardiogram signal, and outputs electrocardiogram data (Step S44). The CPU 16c writes the electrocardiogram data output from the analog-digital converter in the logic circuit 16d into the first ring-buffer (Step S45). The CPU 16c controls the analog-digital converter in the logic circuit 16 so that it repeatedly performs the operations of Step S44 and Step S45 at 150 Hz.

At a second processing, the CPU 16c instructs the analog-digital converter in the acceleration measurement device 11b to start conversion operation (Step S51). The analog-digital converter in the acceleration measurement device 11b accordingly analog-digital converts the acceleration signal, and outputs acceleration data (Step S52). The CPU 16c writes the acceleration data output from the analog-digital converter in the acceleration measurement device 11b into the second ring-buffer (Step S53). The CPU 16c controls the analog-digital converter in the acceleration measurement device 11b so that it performs the operations of Step S52 and Step S53 at 40 Hz.

At a third processing, the CPU 16c instructs the communication device 14 to start transmission operation for the electrocardiogram data and acceleration data (Step S61). The CPU 16c then determines whether the electrocardiogram data and acceleration data are written into the first and second ring-buffers, respectively (Step S62). In the case where the electrocardiogram data and acceleration data are written into the first and second ring-buffers, respectively, the CPU 16c transmits the electrocardiogram data and acceleration data to the hospital computer 50 via the communication device 14 (Step S63). The CPU 16c controls the communication device 14 so that it repeatedly operates the operations of Step 62 and Step 63.

In the case where the electrocardiogram data and acceleration data are not written into the first and second ring-buffers, respectively, the CPU 16c waits until the electrocardiogram data and acceleration data are written into the first and second ring-buffers, respectively.

Figure 15:
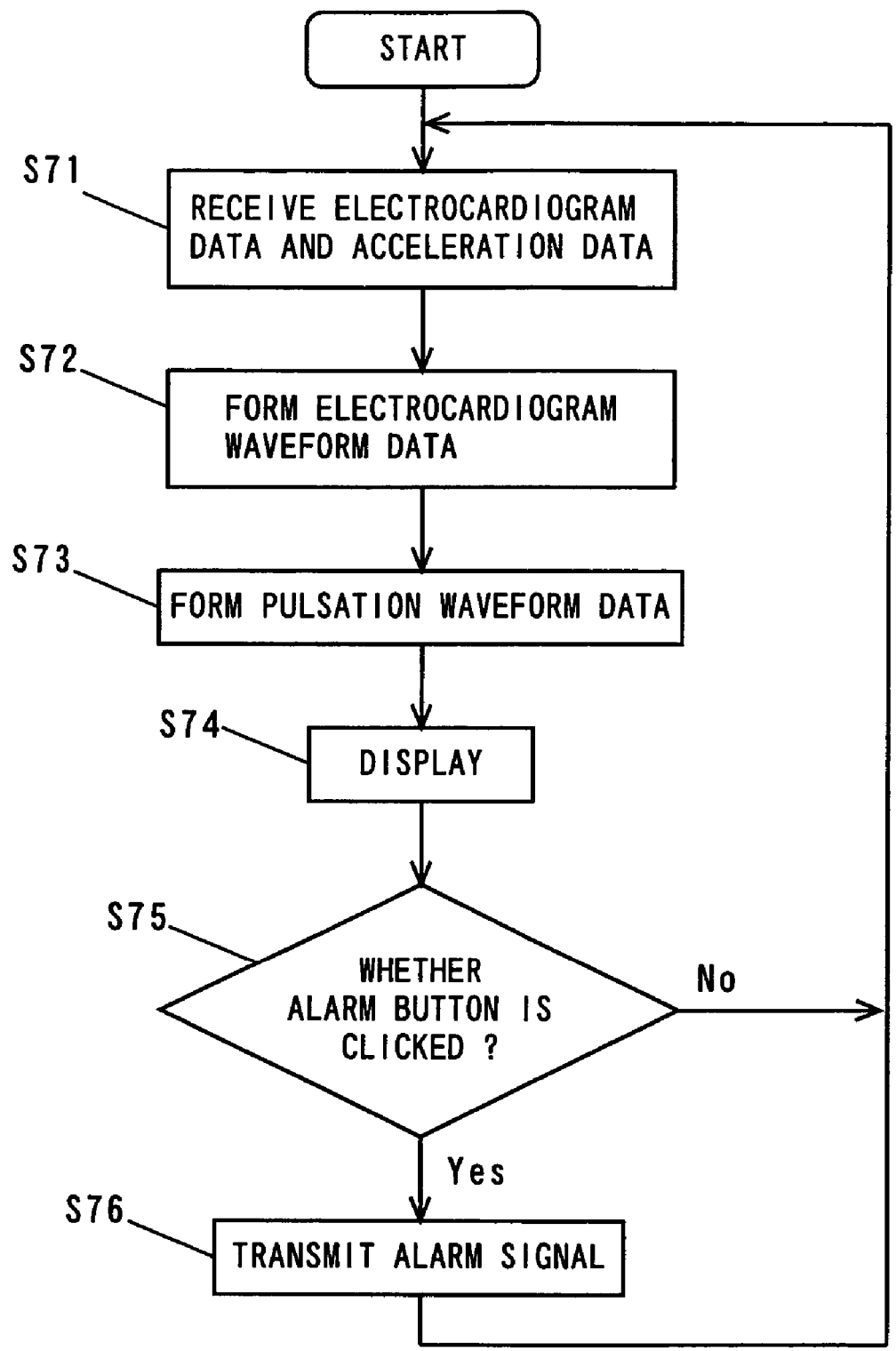
FIG. 15 is a flow chart showing the processing operation of the hospital computer according to the electrocardiogram monitoring program.

FIG. 15 is a flow chart showing the processing operation of the hospital computer according to the electrocardiogram monitoring program.

First, the CPU 501 in the hospital computer 50 receives the electrocardiogram data and acceleration data transmitted from the portable electrocardiograph 10 via the TA 40 and interface unit 506 (Step S71).

The CPU 501 forms the electrocardiogram waveform data described in FIG. 10 (a) based on the received electrocardiogram data (Step S72). The CPU 501 subsequently forms the pulsation waveform data described in FIG. 10 (b) based on the received electrocardiogram data (Step S73).

Then, the CPU 501 displays as shown in FIGS. 10 and 11, for example, on the display device 507 in the hospital computer 50 based on the electrocardiogram diagram waveform data, pulsation waveform data, and acceleration data (Step S74).

After that, the CPU 501 determines whether the alarm button is clicked (Step S75). In the case where the alarm button is clicked, the CPU 501 transmits an alarm signal for instructing the patient to stop the exercise to the portable electrocardiograph of the patient via the interface unit 506 and TA 40 (Step S76), and then returns to Step S71 to receive the electrocardiogram data and acceleration data.

In the case where the alarm button is not clicked at Step S75, the CPU 501 returns to Step S71 to receive the electrocardiogram data and acceleration data.

In the electrocardiogram monitoring system according to the present embodiment, real time and centralized monitoring of the electrocardiograms and accelerations of a plurality of patients can be realized. Therefore, when a patient measures an electrocardiogram using the portable electrocardiograph 10 in every day life, the diagnostician can monitor the electrocardiogram and acceleration of the patient in real time and can immediately stop the patient's exercise when he/she is in bad condition. In addition, the diagnostician can perform real time and centralized monitoring of the electrocardiograms and accelerations of a plurality of patients during their therapeutic exercises in the hospital.

Second Embodiment

Figure 16:
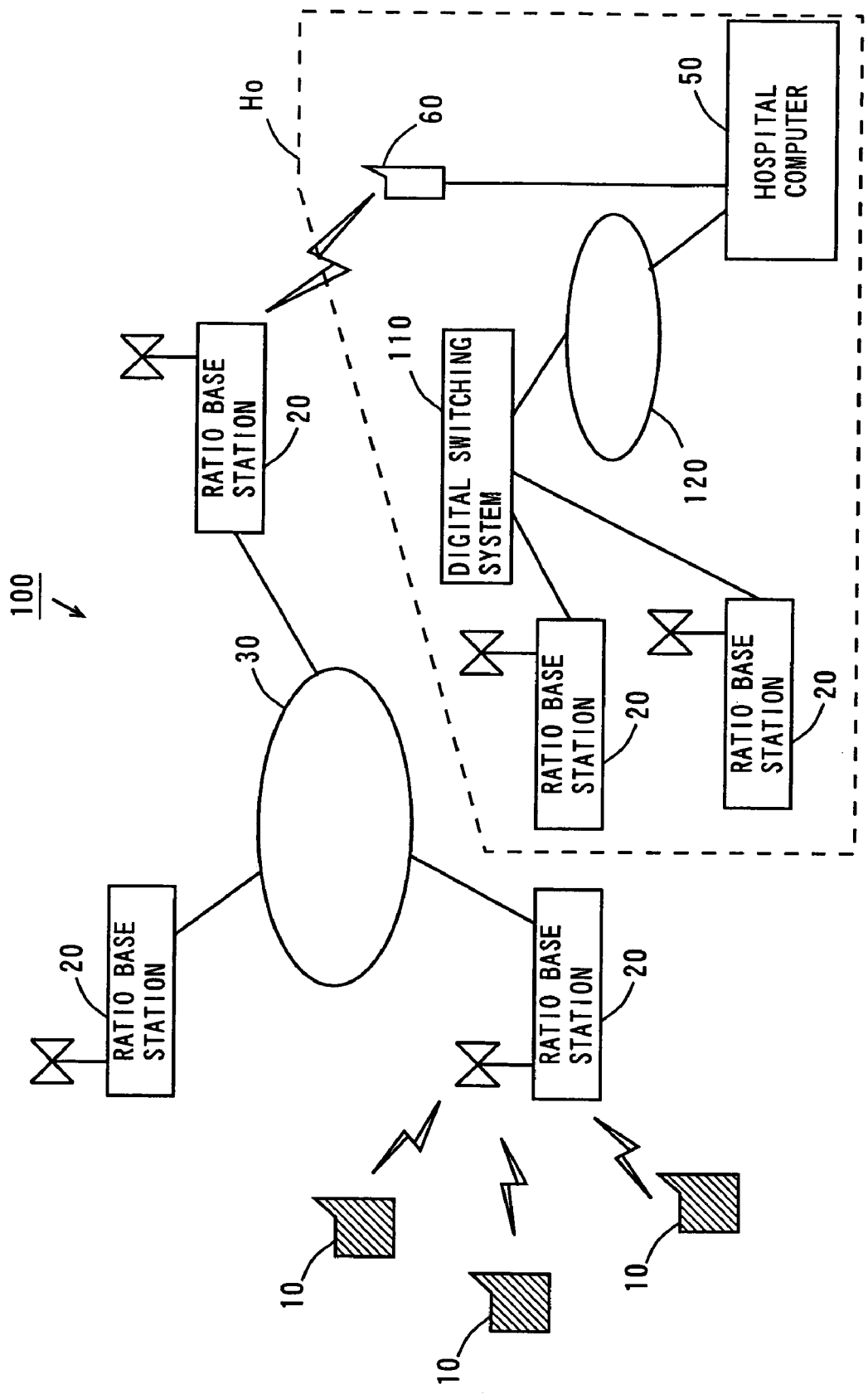
FIG. 16 is a block diagram showing the structure of an electrocardiogram monitoring system using a portable electrocardiograph according to a second embodiment.

FIG. 16 is a block diagram showing the structure of an electrocardiogram monitoring system using a portable electrocardiograph according to a second embodiment.

As shown in FIG. 16, an electrocardiogram monitoring system 100 according to the second embodiment comprises portable electrocardiographs 10, a plurality of radio base stations 20, a public network 30, a hospital computer 50, a radio communication device 60, a digital switching system 110, and a private network 120. The radio communication device 60 is, for example, a PHS. In a hospital Ho, the plurality of radio base stations 20, hospital computer 50, radio communication device 60, digital switching system 110, and private network 120 are provided.

The electrocardiogram data and acceleration data obtained by the portable electrocardiograph 10 of each patient outside the hospital Ho are transmitted to the radio base station 20, and transmitted from the radio base station 20 via the public network 30 to the other radio base station 20, and then transmitted from the other radio base station 20 to the radio communication device 60 to reach the hospital computer 50. The electrocardiograms and accelerations of a plurality of patients are displayed on the screen of the hospital computer 50 in real time based on the electrocardiogram data and acceleration data.

In the case where a patient carries out therapeutic exercise inside the hospital Ho, the electrocardiogram data and acceleration data obtained by the portable electrocardiograph 10 of the patient are transmitted to the radio base station 20 in the hospital Ho, and transmitted from the radio base station 20 via the digital switching system 110 and private network 120 to the hospital computer 50. The electrocardiograms and accelerations of a plurality of patients are displayed on the screen of the hospital computer 50 in real time based on the electrocardiogram data and acceleration data.

The diagnostician thus makes a diagnosis while performing real time and centralized monitoring of the electrocardiograms and accelerations of the plurality of patients which are displayed on the screen of the hospital computer. In the case where any of the patients is in bad condition, the diagnostician transmits an alarm signal via the radio communication device 60, radio base station 20, public network 30, and other radio base station 20 to the portable electrocardiograph 10 of the patient outside the hospital Ho by operating the hospital computer 50, so that he/she can stop the patient's exercise. Alternatively, the diagnostician transmits an alarm signal via the private network 120, digital switching system 110, and radio base station 20 to the portable electrocardiograph 10 of the patient inside the hospital Ho by operating the hospital computer 50, so that he/she can stop the patient's exercise.

Also in the electrocardiogram monitoring system according to the present embodiment, real time and centralized monitoring of the electrocardiograms and accelerations of a plurality of patients can be realized. Therefore, when a patient measures an electrocardiogram using the portable electrocardiograph 10 in every day life, the diagnostician monitors the electrocardiogram and acceleration of the patient in real time and can immediately stop the patient's exercise when he/she is in bad condition. In addition, the diagnostician can perform real time and centralized monitoring of the electrocardiograms and accelerations of a plurality of patients during their therapeutic exercises in the hospital.

Third Embodiment

Figure 17:
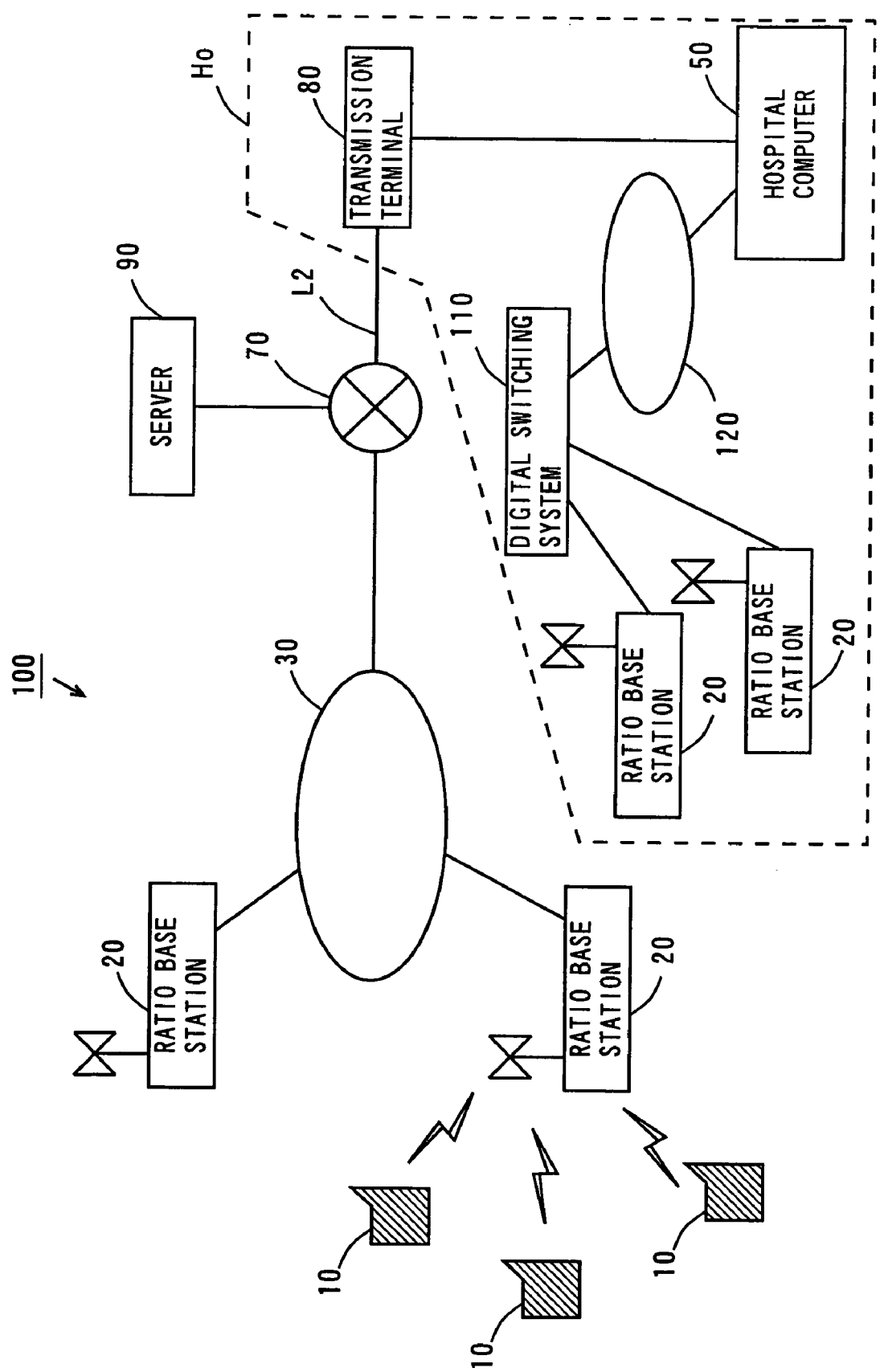
FIG. 17 is a block diagram showing the structure of an electrocardiogram monitoring system using a portable electrocardiograph according to a third embodiment.

FIG. 17 is a block diagram showing the structure of an electrocardiogram monitoring system using a portable electrocardiograph according to a third embodiment.

As shown in FIG. 17, the electrocardiogram monitoring system 100 according to the third embodiment comprises portable electrocardiographs 10, a plurality of radio base stations 20, a public network 30, a hospital computer 50, an Internet 70, a communication terminal 80, a server 90 of an Internet provider, a line L2, a digital switching system 110, and a private network 120. The communication terminal 80 is, for example, a modem. In a hospital Ho, the plurality of radio base stations 20, hospital computer 50, communication terminal 80, digital switching system 110, and private network 120 are provided.

The electrocardiogram data and acceleration data obtained by the portable electrocardiograph 10 of each patient outside the hospital Ho are transmitted to the radio base station 20, and transmitted from the radio base station 20 via the public network 30 and Internet 70 to the server 90 to be stored therein. The hospital computer 50 obtains the electrocardiogram data and acceleration data stored in the server 90 by accessing the server 90 via the communication terminal 80, line L2, and Internet 70. The electrocardiograms and accelerations of a plurality of patients are displayed on the screen of the hospital computer 50 in real time based on the electrocardiogram data and acceleration data.

In the case where a patient carries out therapeutic exercise inside the hospital Ho, the electrocardiogram data and acceleration data obtained by the portable electrocardiograph 10 of the patient are transmitted to the radio base station 20 in the hospital Ho, and transmitted from the radio base station 20 via the digital switching system 110 and private network 120 to the hospital computer 50. The electrocardiograms and accelerations of a plurality of patients are displayed on the screen of the hospital computer 50 in real time based on the electrocardiogram data and acceleration data.

The diagnostician thus makes a diagnosis while performing real time and centralized monitoring of the electrocardiograms and accelerations of the plurality of patients which are displayed on the screen of the hospital computer. In the case where any of the patients is in bad condition, the diagnostician transmits an alarm signal via the communication terminal 80, line L, Internet 70, server 90, public network 30, and radio base station 20 to the portable electrocardiograph 10 of the patient outside the hospital Ho by operating the hospital computer 50, so that he/she can stop the patient's exercise.

Alternatively, the diagnostician transmits an alarm signal via the private network 120, digital switching system 110, and radio base station 20 to the portable electrocardiograph 10 of the patient inside the hospital Ho by operating the hospital computer 50, so that he/she can stop the patient's exercise.

Also in the electrocardiogram monitoring system according to the present embodiment, real time and centralized monitoring of the electrocardiograms and accelerations of a plurality of patients can be realized. Therefore, when a patient measures an electrocardiogram using the portable electrocardiograph 10 in every day life, the diagnostician monitors the electrocardiogram and acceleration of the patient in real time and can immediately stop the patient's exercise when he/she is in bad condition. In addition, the diagnostician can perform real time and centralized monitoring of the electrocardiograms and accelerations of a plurality of patients during their therapeutic exercises in the hospital.

Other Examples of Electrocardiogram Monitoring System

The portable electrocardiograph 10 shown in FIG. 3 may also be used, for example, in a following electrocardiogram monitoring system.

FIG. 18 is a block diagram showing another example of the structure of the electrocardiogram monitoring system using the portable electrocardiograph shown in FIG. 3.

The electrocardiogram monitoring system 100 shown in FIG. 18 comprises portable electrocardiographs 10, a radio base station 20, a public network 30, a TA (Terminal Adapter) 40, a hospital computer 50, and a line L. The line L is, for example, an ISDN line.

The electrocardiogram monitoring system 100 shown in FIG. 18 differs from the electrocardiogram monitoring systems 100 according to the first to third embodiments in that it excludes the digital converter 100, private network 120, and so on.

In this case, the electrocardiogram data and acceleration data obtained by the portable electrocardiograph 10 of each of the patients Y shown in FIG. 1 are transmitted to the radio base station 20, and transmitted from the radio base station 20 via the public network 30, line L, and TA 40 to the hospital computer 50. The electrocardiograms and accelerations of the plurality of patients Y are displayed in real time on the screen of the hospital computer 50.

The diagnostician thus makes a diagnosis while performing real time and centralized monitoring of the electrocardiograms and accelerations of the plurality of patients displayed on the screen of the hospital computer 50. In the case where any of the patients is in bad condition, the diagnostician transmits an alarm signal via the TA 40, line L, public network 30, and radio base station 20 to the portable electrocardiograph 10 of the patient by operating the hospital computer 50, so that he/she can stop the patient's exercise.

Therefore, real time and centralized monitoring of the electrocardiograms and accelerations of a plurality of patients can be realized, also in the case where the portable electrocardiograph 10 shown in FIG. 3 is applied to the electrocardiogram monitoring system 100 excluding the digital switching system 110, private network 120, and so on.

As a result, when a patient measures an electrocardiogram using the portable electrocardiograph 10 in every day life, the diagnostician monitors the electrocardiogram and acceleration of the patient in real time and can immediately stop the patient's exercise when he/she is in bad condition. In addition, the diagnostician can perform real time and centralized monitoring of the electrocardiograms and accelerations of a plurality of patients during their therapeutic exercises in the hospital.

In the above-described first to third embodiments, the RAM 16a corresponds to a storage device, the first multi-layered circuit board P1 and second multi-layered circuit board P2 correspond to stacked-layered circuit boards, the ground planes GP1, GP2 correspond to ground conductor layers, the circuit board layers EP correspond to circuit boards, the communication device 14 and PHS correspond to radio communication devices, the TA 40, radio communication device 60, and communication terminal 80 correspond to communication devices. The buzzer 19a and the lamp 19b correspond to an alarm output unit, the buzzer 19a corresponds to an alarm sound output device, and the lamp 19b corresponds to an alarm display device. The RAM 16a corresponds to a first storage device and a second storage device.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A portable electrocardiograph comprising:
    first and second stacked-layered circuit boards;
    an electrocardiogram measurement device that measures an electrocardiogram to obtain electrocardiogram data; and
    a radio communication device that radio-transmits the electrocardiogram data obtained by said electrocardiogram measurement device in real time; and
    a logic circuit that analog-digital converts said electrocardiogram data, wherein
    said first and second stacked-layered circuit boards each include a plurality of circuit boards and a ground conductor layer provided between any ones of said plurality of circuit boards,
    said logic circuit is arranged between one side of said first stacked-layered circuit board and one side of said second stacked-layered circuit board,
    said electrocardiogram measurement device is arranged on the other side of said first stacked-layered circuit board, and said radio communication device is arranged on the other side of said second stacked-layered circuit board,
    said ground conductor layer is disposed so that said electrocardiogram measurement device and said radio communication device are isolated from each other, and
    said radio communication device includes a transmission circuit.

2. The portable electrocardiograph according to claim 1, further comprising a casing that houses said electrocardiogram measurement device, said radio communication device, and said stacked-layered circuit board.

3. The portable electrocardiograph according to claim 1, further comprising an externally readable first storage device that stores the electrocardiogram data obtained by said electrocardiogram measurement device.

4. The portable electrocardiograph according to claim 1, further comprising an accelerometer that measures acceleration to obtain acceleration data, wherein said radio communication device radio-transmits the acceleration data obtained by said accelerometer in real time.

5. The portable electrocardiograph according to claim 4, further comprising an externally readable second storage device that stores the acceleration data obtained by said accelerometer.

6. The portable electrocardiograph according to claim 1, wherein said radio communication device receives a given alarm signal that is transmitted by an external computer, the portable electrocardiograph further comprising an alarm sound output device that outputs an alarm sound in response to the alarm signal received by said radio communication device.

7. The portable electrocardiograph according to claim 1, wherein said radio communication device receives a given alarm signal that is transmitted by an external computer, the portable electrocardiograph further comprising an alarm display device that displays an alarm in response to the alarm signal received by said radio communication device.

8. The portable electrocardiograph according to claim 1, wherein said radio communication device is a personal handheld device.

9. The portable electrocardiograph according to claim 8, wherein said personal handheld device is a cellular phone.

* * * * *